US011981886B2

(12) United States Patent
Cornu et al.

(10) Patent No.: US 11,981,886 B2
(45) Date of Patent: May 14, 2024

(54) BIOCOMPATIBLE THREE-DIMENSIONAL NETWORK AND USE THEREOF AS A CELL SUPPORT

(71) Applicants: UNIVERSITE DE MONTPELLIER, Montpellier (FR); INSTITUT NATIONAL DE LA SANTE ET DE LA RECHERCHE MEDICALE, Paris (FR); CENTRE NATIONAL DE LA RECHERCHE SCIENTIFIQUE, Paris (FR); ECOLE NATIONALE SUPERIEURE DE CHIMIE DE MONTPELLIER, Montpellier (FR)

(72) Inventors: David Cornu, Prades-le-Lez (FR); Norbert Bakalara, Saint-Martin-de-Londres (FR); Emilie Marhuenda, Montpellier (FR); Ali Saleh, Montpellier (FR)

(73) Assignees: UNIVERSITE DE MONTPELLIER, Montpellier (FR); INSERM (INSTITUT NATIONAL DE LA SANTE ET DE LA RECHERCHE MEDICALE), Paris (FR); CENTRE NATIONAL DE LA RECHERCHE SCIENTIFIQUE, Paris (FR); ECOLE NATIONALE SUPERIEURE DE CHIMIE DE MONTPELLIER, Montpellier (FR)

( * ) Notice: Subject to any disclaimer, the term of this patent is extended or adjusted under 35 U.S.C. 154(b) by 927 days.

(21) Appl. No.: 16/969,497

(22) PCT Filed: Feb. 15, 2019

(86) PCT No.: PCT/EP2019/053883
§ 371 (c)(1),
(2) Date: Aug. 12, 2020

(87) PCT Pub. No.: WO2019/158724
PCT Pub. Date: Aug. 22, 2019

(65) Prior Publication Data
US 2020/0377837 A1 Dec. 3, 2020

(30) Foreign Application Priority Data
Feb. 16, 2018 (FR) ...................................... 1851324

(51) Int. Cl.
C12M 1/12 (2006.01)
C08L 33/18 (2006.01)
C12N 5/00 (2006.01)
D01D 5/00 (2006.01)
D01D 10/02 (2006.01)
D01F 6/18 (2006.01)
D06M 15/15 (2006.01)

(52) U.S. Cl.
CPC ............. *C12M 25/14* (2013.01); *C08L 33/18* (2013.01); *C12N 5/0068* (2013.01); *D01D 5/0038* (2013.01); *D01D 10/02* (2013.01); *D01F 6/18* (2013.01); *D06M 15/15* (2013.01); *C12N 2513/00* (2013.01); *C12N 2533/30* (2013.01); *C12N 2533/90* (2013.01); *C12N 2539/10* (2013.01)

(58) Field of Classification Search
CPC ...... C12M 25/14; C08L 33/18; C12N 5/0068; C12N 2513/00; C12N 2533/30; C12N 2533/90; C12N 2539/10; D01D 5/0038; D01D 10/02; D01F 6/18; D06M 15/15
USPC ......................................................... 526/342
See application file for complete search history.

(56) References Cited

FOREIGN PATENT DOCUMENTS

JP 2007319074 A 12/2007
KR 20160042631 A 4/2016

OTHER PUBLICATIONS

Pan et al. "Preparation and Characterization of Electrospun PLCL/Poloxamer Nanofibers and Dextran/Gelatin Hydrogels for Skin Tissue Engineering", PLOS One, www.plosone.org, 2014, vol. 9, Issue 11, e112885 (Year: 2014).*
Oliveira et al. "A statistical approach to evaluate the oxidative process of electrospun polyacrylonitrile ultrathin fibers", J. Appl. Polym. Sci. 2017, 134, 45458 (Year: 2017).*
Su et al. "Optimum Heat Treatment Conditions for PAN-based Oxidized Electrospun Nonwoven", Fibers and Polymers, 2012, vol. 13, No. 1, 38-43 (Year: 2012).*
Eren et al. "Composite Nanofibers of Polyacrylonitrile (PAN) and Amino-functionalized Carbon Nanotubes Electrospun from Dimethylsulfoxide", Marmara Journal of Pure and Applied Sciences, 2015, Special Issue 1, 95-98 (Year: 2015).*
Yordem et al. "Effects of electrospinning parameters on polyacrylonitrile nanofiber diameter: An investigation by response surface methodology", Materials and Design, vol. 29 (2008) 34-44 (Year: 2008).*
Li et al. "Electrospun nanofibrous structure: A novel scaffold for tissue engineering", J. Biomed. Mater., Res 60, 2002, 613-621 ( Year: 2002).*
Eren, O., et al., "Composite Nanofibers of Polyacrylonitrile (PAN) and Amino-functionalized Carbon Nanotubes Electrospun from Dimethylsulfoxide," Marmara Journal of Pure and Applied Sciences, 2015, Special Issue-1, pp. 95-98.
French Search Report from French Patent Application No. 1851324, dated Feb. 16, 2018.

(Continued)

*Primary Examiner* — Michael M. Bernshteyn
(74) *Attorney, Agent, or Firm* — Greer, Burns & Crain, Ltd

(57) ABSTRACT

An infusible three-dimensional network of crosslinked acrylic-type polymer fibers, where the diameter of the fibers is between 0.1 and 1.5 μm, the size of the interstices between the fibers is between 0.1 and 50 μm² and the stiffness of the network includes an elastic modulus between 0.01 and 10,000 kPa.

20 Claims, 7 Drawing Sheets

(56) References Cited

OTHER PUBLICATIONS

International Search Report and Written Opinion for PCT/EP2019/053886 dated May 13, 2019.

Li, W., et al., "Electrospun nanofibrous structure: A novel scaffold for tissue engineering," Wiley Periodicals XP001183765, 2001, pp. 613-621.

Oliveira Jr., M., et al., "A statistical approach to evaluate the oxidative process of electrospun polyacrylonitrile ultrathin fibers," Journal of Applied Polymer Science, 2017, 11 pages.

Pan, J., et al., "Preparation and Characterization of Electrospun PLCL/Poloxamer Nanofibers and Dextran/Gelatin Hydrogels for Skin Tissue Engineering," PLOS One, 2014, vol. 9, No. 11, 12 pages.

Su, C., et al. "Optimum Heat Treatment Conditions for PAN-based Oxidized Electrospun Nonwovens," Fibers and Polymers, 2012, vol. 13, No. 1, pp. 38-43.

Yördem, O., et al., "Effects of electrospinning parameters on polyacrylonitrile nanofiber diameter: An investigation by response surface methodology," Materials and Design 29, 2008, pp. 34-44.

\* cited by examiner

BIOCOMPATIBLE THREE-DIMENSIONAL NETWORK AND USE THEREOF AS A CELL SUPPORT

BACKGROUND

The present invention relates to the field of biocompatible three-dimensional devices.

The subject of the invention is a three-dimensional (3D) network of biocompatible fibres, and its form when integrated in a device, another subject is a process for manufacturing such a network of fibres. Another subject of the invention is the use of said network as a cell support for the study of cell behaviours within a 3D environment, in particular the survival, proliferation, migration and invasiveness of the cells.

Networks and devices simulating the physical properties of in vivo cell migration conditions in two dimensions are frequently used and marketed. Several types of 3D networks or devices are being developed; the networks that are currently known are constituted by a material such as decellularized tissues, layers of cells, hydrogels, electrospun fibres and sponges, and have various drawbacks according to the nature of the material used.

Shogolu et al. ("*Recreating complex pathophysiologies in vitro with extracellular matrix surrogates for anticancer therapeutics screening*", Drug Discov. Today, vol. 21, No. 9, p. 1521-31, 2016) describes different 3D devices mimicking the in vitro microenvironment of tumours and cites their drawbacks: intact decellularized tissues are difficult to obtain and do not allow sufficient standardization and reproducibility, cell monolayers, hydrogels can have a significant cytotoxicity, electrospun fibres do not allow a good cellular infiltration, sponges do not allow a control of the rigidity, degradation or porosity of the network.

Bui et al. ("*Brain tumor genetic modification yields increased resistance to paclitaxel in physical confinement*", Nature Sci. Reports 6:26134, 2016) describes a polydimethylsiloxane (PDMS) microfluidic device generating three different degrees of physical confinement: a narrow confinement (5×5 µm), wide confinement (15×15 µm) and 2D confinement (height of 150 µm). This device is coated with laminin before use. This system is stiff and the interactions of the cells with the faces of the support are flat, as in 2D.

Akhmanova et al. ("*Physical, spatial and molecular aspects of extracellular matrix of in vivo niches and artificial scaffolds relevant to stem cells research*", Stem Cells International, Vol. 2015, article ID 167025, 2015) describes devices comprising electrospun fibres constituted by polyvinyl alcohol (PVA), polydimethylsiloxane (PDMS), polyethylene glycol dimethacrylate (PEGdma), polyethylene oxide (PEO), polycaprolactone (PCL), polyurethane (PU), polyacrylamide (PAA).

Lee et al. ("*Plasma treated flexible aminoclay-decorated electrospun nanofibres for neural stem cell self-renewal*", J. Nanosci. Nanotechnol., February 16(2): 1392-5, 2016) describes nanofibres obtained by electrospinning of polyacrylonitrile (PAN) and comprising magnesium or iron aminoclays.

Liu et al. ("Electrospun polyacrylonitrile-based nanofibres maintain embryonic stem cell stemness via TGF-beta signaling" J Biomed Nanotechnol. April; 12(4):732-42, 2016) describes a cell culture device constituted by biocompatible PAN fibres treated by electrospinning.

Mahmoudifard M. et al. ("*The different fate of satellite cells on conductive composite electrospun nanofibres with graphene and graphene oxide nanosheets*", Biomed Mater. March 10; 11(2) 2016) describes a network of polyaniline (PANI) and PAN fibres, supplemented by nanosheets of graphene or graphene oxide.

Jain et al. ("*Biomaterials for liver tissue engineering*" Hepatol Int. April; 8(2):185-97, 2014) studies the in vitro cytocompatibility of polyacrylonitrile (PAN), in the form of carbon nanofibres or thin films.

US 2016/0377600 describes a 3D network synthesized by electrospinning a biofunctional composition comprising a polymer and proteins. After electrospinning, the network is placed directly in a vacuum chamber and stored under dry atmosphere before use.

US 2016/0355780 describes a 3D microenvironment suitable for cell culture, prepared by combining at least one natural or synthetic polymer and an integrin-activating peptide motif. Said 3D network is obtained by electrospinning of a biofunctional composition. After electrospinning, the network is placed directly in a vacuum chamber and stored under dry atmosphere before use.

The subject of US 2012/0040581 is a specific process for producing nanofibre networks comprising the use of predefined moulds.

The currently known networks constituted by electrospun fibres are characterized by a low infiltration and low cell growth, non-uniform cell distribution and by the fact that the cells migrate there only independently. In addition, these materials can have a certain toxicity with regard to the cells and do not allow a complete analysis, in particular at the proteomic and functional level, of the migrating cells. In fact, when the networks are constituted by collagen, the cellular protein analysis is disrupted by the salting out during protein extraction of proteins originating from these networks. The opacity of materials such as polycaprolactone requires the specific use of two-photon microscopes to characterize the cells. Finally, it is not possible to carry out an optional modulation of the mechanical properties of a 3D network of the state of the art independently of a chemical modulation of this network, and vice versa, which limits the possibilities of adaptation to different cell types.

The inventors have designed and produced a 3D network constituted by fibres obtained by electrospinning of a solution of acrylic-type polymer, in particular of polyacrylonitrile (PAN), to which a heat treatment is applied, carried out at a temperature above 40° C. and below 400° C., which leads to the aromatization and the crosslinking of the fibres. Surprisingly, said network has mechanical properties very close to the in vivo environment of cells, and biocompatibility, non-toxicity and adhesion-support properties for said cells. In addition, said network has an infusible nature, fluorescence optical properties and residual surface chemical functions allowing the optional subsequent functionalization thereof. The autofluorescent properties of said network of fibres makes it easy to visualize cells within the network, in particular by immunofluorescence or measuring the efflux of cellular calcium measurable by multiphoton microscopy, epifluorescence microscopy or confocal microscopy, using the marked indicators and appropriate analysis software, well known to a person skilled in the art. The possibility of subsequent functionalization of the network makes it possible to study and reproducibly characterize cell behaviours within a 3D environment, in particular the survival, proliferation, migration and invasiveness of the cells.

A 3D network according to the invention has the advantage of being able to independently undergo modulation of its mechanical properties and/or its chemical properties. The mechanical properties of the network can be modified for example by adding carbon nanotubes which increase its stiffness. The chemical properties can be modulated by functionalizing the surface of the fibres, optimizing the mimicking of the substrate/cell interface.

In addition, a network according to the invention is characterized by its non-cytotoxicity, its stability (no salting out of the compounds during extraction of proteins from the cells present within the network) and by an elasticity that can be close to that of a tissue under physiological and pathological conditions ("Tissue Stiffness Dictates Development, Homeostasis, and Disease Progression" *Organogenesis*. 11(1): 1-15, 2015), this elasticity can also be modulated to reach at least 1260 kPa after the addition of carbon nanotubes. A network according to the invention thus makes it possible to mimic the biological environment of the cells as closely as possible.

Depending on the optional functionalization of the fibres and the nature of this functionalization, a 3D network according to the invention makes it possible to study the migration of different cell types. Depositing poly-D-lysine and laminin on the surface of the fibres makes it possible for example to study the individual migration of glioblastoma stem cells (GSCs) when they move collectively over uncoated fibres.

The inventors have shown that, when they are brought into contact with a 3D network according to the invention, cells have migratory behaviours similar to the in vivo migratory behaviours described and they infiltrate within the network with a uniform distribution.

Finally, this network according to the invention makes it possible to visualize and reproducibly measure cell behaviours using microscopy, in particular the migratory behaviours. It also makes it possible to extract proteins that can be analysed by western blot and the possibility of complete analyses, including the transcriptome, the proteome and the metabolomic study etc. The fibres are very easy to use, can be produced rapidly in large quantities and their production is inexpensive.

A 3D network according to the invention is capable of being easily integrated into a device of the "multi-well plate" type for analytical studies or screening studies, according to the nature of the device chosen.

A first subject of the invention is thus an infusible three-dimensional network of crosslinked polymer fibres characterized in that the diameter of said fibres is comprised between 0.1 and 1.5 µm, the size of the interstices between the fibres is comprised between 0.1 and 50 µm$^2$ and the stiffness of the network is characterized by an elastic modulus comprised between 0.01 and 10,000 kPa. This network is capable of being integrated within a device.

A second subject of the invention is a process for preparing a three-dimensional network of crosslinked polymer fibres according to the invention, this process comprising a step of synthesizing a 3D network of fibres by electrospinning, followed by a step of heat treatment of the synthesized 3D network, at a temperature above 40° C. and below 400° C., preferably at a temperature above 200° C. and below 300° C.

A third subject of the invention is the use of a 3D network of crosslinked polymer fibres according to the invention as a cell support, this cell support being used in vitro for the culture of cells and the study of cell behaviours, in particular their survival, their proliferation, their migration and their invasiveness. The cells studied are in particular glioblastoma cells.

This use comprises in particular visualization of the behaviour of the cultivated cells on a network according to the invention, for example by microscopy and biochemical analysis of the cells by any method known to a person skilled in the art.

Finally, a fourth subject of the invention is a test device, such as for example a multi-well plate or a Petri dish, in which a 3D network of fibres according to the invention is inserted, cut to the required dimensions and included in said device, and its use for analytical applications. Other characteristics, advantages and embodiments of the subjects of the invention are detailed in the description below, given by way of illustration and non-limitatively.

In the remainder of the text, the expressions "comprised between . . . and . . . " are inclusive.

DETAILED DESCRIPTION

The first subject of the invention is a three-dimensional network of crosslinked polymer fibres characterized in that:
the diameter of said fibres is comprised between 0.1 and 1.5 µm, preferably between 0.3 and 1 µm, and more preferentially between 0.6 and 0.8 µm,
the size of the interstices between said fibres is comprised between 0.1 and 50 µm$^2$, preferably between 0.5 and 10 µm$^2$, and more preferentially between 1 and 2 µm$^2$, and
the stiffness of said network is characterized by an elastic modulus comprised between 0.01 and 10,000 kPa, preferably between 0.1 and 10,000 kPa, preferably between 0.1 and 1,000 kPa, more preferentially between 0.1 and 300 kPa.

By "crosslinked polymer fibres" is meant a fibrous material comprising a crosslinked polymer, said crosslinked polymer being obtained by applying a suitable heat or optical treatment to a polymer previously organized in the form of fibres. Under the effect of said heat or optical treatment, the polymer adopts a specific 3D structural organization in order to lead to a crosslinked polymer without losing its fibrous morphology. Crosslinking is defined as the formation of a three-dimensional network by bridging of the polymer chains. The nature of the network depends on the thermal or optical stress.

The processes for synthesizing polymer fibres are well known to a person skilled in the art, of which there may be mentioned electrospinning. The processes for crosslinking a plastic polymer by heat or optical treatment are also well known to a person skilled in the art. Of the thermal crosslinking processes, application of a treatment for at least 10 minutes at a temperature comprised between 40 and 400° C. is known to lead to the aromatization of the polymer fibres and the crosslinking thereof. Of the optical crosslinking processes there may be mentioned in particular UV photocrosslinking.

A 3D network of crosslinked polymer fibres according to the invention is biocompatible, infusible and, preferably, insoluble in the usual solvents used in biology, such as in particular water, alcohols or DMSO.

By "biocompatible" is meant a support which does not induce a cytostatic and/or cytotoxic effect with regard to the cells with which it is in contact. A 3D network according to the invention is also preferably non-biodegradable on contact with said cells.

In a 3D network according to the invention, said crosslinked polymer is obtained from:
a polymer solution comprising: at least 10% acrylic such as polyacrylonitrile (PAN) or poly(methyl methacrylate) (PMMA); or at least 10% of a polyamide, for example polyhexamethylene adipamide (PA 6.6 or nylon), or at least 10% of another crosslinkable motif, or a copolymer solution or a mixed solution comprising at least 10% styrene-acrylonitrile copolymer (SAN), or at least 10% of a copolymer or mixture such as acrylonitrile-butadiene-styrene (ABS), butadiene-acrylonitrile (NBR), or at least 10% of another crosslinkable motif.

By "3D network of crosslinked polymer fibres" is meant a network constituted by fibres of which at least the shell, i.e. the surface part, is constituted by a material comprising at least 10% crosslinked polymer, this percentage being expressed in weight percent of said material. The core of said fibres can be constituted by any suitable material, identical to or different from the material constituting the shell of the fibres. According to this aspect, at least the shell of said fibres is constituted by a material comprising at least 10%, at least 20%, at least 30%, at least 40%, at least 50%, at least 60%, at least 70%, at least 80%, or at least 90% crosslinked polymer, this percentage being expressed in weight percent of the material constituting the surface of said fibres. A 3D network according to the invention in which the core and the shell of the fibres are constituted by different materials can in particular be obtained by a co-axial electrospinning process, in which the polymers constituting the shell and the core of said fibres are extruded simultaneously.

According to a particular embodiment, the shell and the core of the fibres of a 3D network according to the invention are constituted by a material comprising at least 10%, at least 20%, at least 30%, at least 40%, at least 50%, at least 60%, at least 70%, at least 80%, or at least 90% crosslinked polymer, this percentage being expressed in weight percent of the material constituting the surface of said fibres.

According to a particular embodiment, said crosslinked polymer is obtained from a polymer comprising at least 10% of a polymer selected from: acrylic-type polymers, such as in particular polyacrylonitrile (PAN), and polyamide-type polymers, said polymers being present in the form of a polymer or a copolymer. More particularly, a 3D network according to the invention is characterized in that the crosslinked polymer is obtained from a solution of acrylic-type polymer, preferably a solution comprising at least 10% acrylic-type polymer. By "acrylic-type polymer" is meant any polymer derived from acrylic acid and its derivatives, such as for example acrylate, esters such as methyl acrylate and acrylonitrile.

According to a particular embodiment, a subject of the invention is thus a three-dimensional network of crosslinked acrylic-type polymer fibres characterized in that:
the diameter of said fibres is comprised between 0.1 and 1.5 µm, preferably between 0.3 and 1 µm, and more preferentially between 0.6 and 0.8 µm,
the size of the interstices between said fibres is comprised between 0.1 and 50 µm$^2$, preferably between 0.5 and 10 µm$^2$, and more preferentially between 1 and 2 µm$^2$, and
the stiffness of said network is characterized by an elastic modulus comprised between 0.01 and 10,000 kPa, preferably between 0.1 and 10,000 kPa, preferably between 0.1 and 1,000 kPa, more preferentially between 0.1 and 300 kPa.

According to a particular example, said plastic polymer comprises at least 50% PAN, the percentage of PAN being expressed as a percentage of the total weight of the different polymers.

According to this particular aspect, said 3D network is constituted by fibres the core of which is constituted by any suitable material such as in particular a polymer, or a gel.

According to a more particular aspect of a 3D network according to the invention, said fibres are entirely constituted by a crosslinked polymer. According to this aspect, a 3D network according to the invention is constituted by fibres comprising at least 10%, at least 20%, at least 30%, at least 40%, at least 50%, at least 60%, at least 70%, at least 80%, or at least 90% crosslinked polymer, this percentage being expressed in weight percent of said fibres.

According to another particular embodiment, a 3D network according to the invention is constituted by crosslinked polymer fibres, said crosslinked polymer comprising at least one stiffening compound, said stiffening compound preferably being selected from the nanofillers, and more preferentially from: nanoparticles, nanotubes, nanofibres and nanosheets.

According to a particular embodiment, a network according to the invention is constituted by fibres comprising at least 10%, at least 20%, at least 30%, at least 40%, at least 50%, at least 60%, at least 70%, at least 80%, or at least 90% PAN-derived crosslinked polymer, this percentage being expressed in weight percent of the PAN solution before crosslinking thereof.

According to a particular aspect, the diameter of the fibres of a 3D network according to the invention is comprised between 0.1 and 1.5 µm, preferably between 0.2 and 1.2 µm, preferably between 0.3 and 1.1 µm, preferably between 0.4 and 1 µm, preferably between 0.5 and 0.9 µm, and more preferentially between 0.6 and 0.8 µm, this value representing the average of the diameters of the fibres measured within said network. Said diameter is measured by any means known to a person skilled in the art, and in particular by scanning electron microscopy.

By "interstice between said fibres" is meant the free space, or "pore" or "mesh" situated between at least two fibres of the network, in which at least one cell, when it is brought into contact with said network, is capable of being placed. In a 3D network according to the invention, before any optional functionalization of the surface of the fibres, the size of the interstices is the average dimension of the surface of said interstices, this size is comprised between 0.1 and 50 µm$^2$, preferably between 1 and 10 µm$^2$, and more preferentially between 1 and 2 µm$^2$. This dimension is measured in particular by electron microscopy or confocal optical microscopy. According to another definition, the porosity of a network according to the invention is defined by a filtration threshold comprised between 0.1 and 50 µm, preferably between 1 and 10 µm, and more preferentially between 1 and 2 µm. This dimension is defined before any optional functionalization of the surface of the fibres such as for example their being coated with a protein of the extracellular matrix, said functionalization not substantially modifying the size of the interstices between the fibres.

By "stiffness" is meant a characteristic defined by the elastic modulus. The stiffness of a network according to the invention is characterized by an elastic modulus comprised between 0.01 and 10,000 kPa, preferably between 0.1 and 10,000 kPa, preferably between 0.1 and 1,000 kPa, preferably between 0.1 kPa and 300 kPa. The elastic modulus is measured by any means known to a person skilled in the art, and in particular by atomic force microscopy, utilizing application of a force varying from the picoNewton to the nanoNewton. Preferably, and unless otherwise indicated, the stiffness is measured as an average value over the entire recorded image. Alternatively, the stiffness can be measured with regard to the fibres themselves, excluding the interstices between the fibres.

According to a particular aspect, a 3D network according to the invention is characterized by fibres that are aligned with one another, or in a general orientation but without necessarily being strictly parallel. According to another particular aspect, a 3D network according to the invention is characterized by fibres that are organized randomly.

According to a more particular aspect, a subject of the invention is a 3D network of crosslinked polymer fibres obtained by thermal crosslinking of a solution of acrylic-type polymer. According to a more particular aspect of the invention, said solution comprises an acrylic-type polymer to the exclusion of any other polymer. According to another more particular aspect, said solution comprises an acrylic-type polymer and a second polymer. According to an even more particular aspect of the invention, said solution comprises a first acrylic-type polymer and a second acrylic-type polymer.

According to a more particular aspect, a subject of the invention is a 3D network of crosslinked polymer fibres obtained by the thermal crosslinking of a polyacrylonitrile (PAN) solution. According to a more particular aspect of the invention, said solution comprises PAN to the exclusion of any other polymer, according to another more particular aspect, said solution comprises PAN in the form of a copolymer.

By "polyacrylonitrile" is meant a compound of formula $(C_3H_3N)n$ of formula (I) below:

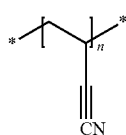

(I)

According to a more particular aspect, a 3D network according to the invention is constituted by fibres the surface of which comprises at least 10%, at least 20%, at least 30%, at least 40%, at least 50%, at least 60%, at least 70%, at least 80%, at least 90%, at least 95% or at least 98% crosslinked polymer obtained by thermal crosslinking of PAN, said percentage being expressed in weight percent of the surface of said fibres.

According to an even more particular aspect, a 3D network according to the invention is constituted by fibres comprising at least 10%, preferably at least 20%, at least 30%, at least 40%, at least 50%, at least 60%, at least 70%, at least 80%, at least 90%, at least 95% or at least 98% crosslinked polymer obtained by thermal crosslinking of PAN, this percentage being expressed in weight percent of said fibres.

According to another particular aspect, a 3D network according to the invention has fluorescence properties, in particular at the following wavelengths: in the green (488 nm) and red (594 nm), and to a lesser extent in the blue (350 nm) and in the infrared (647 nm). These properties are measurable in particular by fluorescence microscopy, by excitation at 488, 594, 350 and/or 647 nm. These properties are also measurable by the technique called Lambda scan technique, for example by applying an excitation to the material at the excitation wavelengths 405, 458, 488, 524, 561 and/or 633 nm, then determining the wavelength and the intensity of the signal emitted.

According to a particular aspect, a subject of the invention is a 3D network of crosslinked polymer characterized in that:
said crosslinked polymer is obtained by thermal crosslinking of a polyacrylonitrile solution,
the diameter of said fibres is comprised between 0.1 and 1.5 µm, preferably between 0.3 and 1 µm, and more preferentially between 0.6 and 0.8 µm,
the size of the interstices between said fibres is comprised between 0.1 and 50 µm$^2$, preferably between 0.5 and 10 µm$^2$, and more preferentially between 1 and 2 µm$^2$, and
the stiffness of said network is characterized by an elastic modulus comprised between 0.1 and 10,000 kPa, preferably between 0.1 and 300 kPa,
optionally, the surface of the fibres is coated with at least one protein of the extracellular matrix. Of these proteins there may be mentioned in particular laminin, fibronectin, vitronectin, hyaluronic acid and collagen.

According to an even more particular aspect, a subject of the invention is a 3D network of crosslinked polymer characterized in that:
said crosslinked polymer is obtained by thermal crosslinking of a polyacrylonitrile solution,
the diameter of said fibres is comprised between 0.6 and 0.8 µm,
the size of the interstices between said fibres is comprised between 1 and 2 µm$^2$, and
the stiffness of said network is characterized by an elastic modulus comprised between 0.1 and 10,000 kPa, preferably between 0.1 and 300 kPa,
optionally, the surface of the fibres is coated with at least one protein of the extracellular matrix, in particular laminin.

According to this even more particular aspect, said 3D network of fibres is suitable as a support for glioblastoma cells.

According to an even more particular aspect, a subject of the invention is a 3D network of crosslinked polymer fibres, characterized in that said polymer comprises a stiffening compound. Such a stiffening compound is preferably selected from the compounds well known for this purpose to a person skilled in the art. It can in particular be selected from nanofillers, and preferably from: nanoparticles, nanotubes, nanofibres and nanosheets. More preferentially, said stiffening compound is selected from carbon nanotubes, in particular multi-walled carbon nanotubes (MWCTs) which can be easily dispersed by a person skilled in the art in a solvent suitable for the polymer, said nanotubes being able to be surface-functionalized by —COOH or —NH$_2$ functions in order to promote their dispersion. According to this aspect, said stiffening compound is present within said crosslinked polymer, it is thus not added to the 3D network after the synthesis thereof, but, quite the opposite, it is incorporated in the polymer.

According to a particular aspect, at least the shell of said fibres of the network comprises said crosslinked polymer incorporating a stiffening compound, at a concentration of stiffening compound comprised between 0.00001 and 5%, preferably between 0.00001 and 1%, preferably between 0.0001 and 0.1%, preferably between 0.0002 and 0.08%, preferably between 0.00075 and 0.05%, expressed in weight percent of the solution of said polymer before crosslinking.

According to a more particular aspect, said stiffening compound is present within the material constituting the shell and the core of said fibre.

According to an even more particular aspect, a subject of the invention is a 3D network of crosslinked polymer fibres characterized in that the surface of said fibres is coated with at least one protein of the extracellular matrix. Of the proteins of the extracellular matrix there may be mentioned in particular laminin, fibronectin, vitronectin, hyaluronic acid and collagen.

By "fibre coated with at least one protein" is meant a fibre on the surface of which a protein is present, at a protein density greater than or equal to 10 µg/cm$^2$. As observed using microscopy, said proteins can be present discontinuously at the surface of said fibres.

According to a particular aspect, a 3D network of crosslinked polymer fibres according to the present invention is characterized in that the surface of the fibres of the network is coated with at least one protein of the extracellular medium, preferably laminin.

According to a particular aspect, a 3D network of crosslinked polymer fibres according to the present invention is characterized in that:
  said crosslinked polymer is obtained by thermal crosslinking of PAN,
  the diameter of the fibres is comprised between 0.1 and 1.5 µm, preferably between 0.3 and 1 µm, and more preferentially between 0.6 and 0.8 µm,
  the average size of the interstices between the fibres is comprised between 0.1 and 50 µm$^2$, preferably between 0.5 and 10 µm$^2$, more preferentially between 1 and 2 µm$^2$,
  the stiffness of said network is characterized by an elastic modulus comprised between 0.01 and 10,000 kPa, preferably between 0.1 and 10,000 kPa, preferably between 0.01 kPa and 1,000 kPa, preferably between 0.1 kPa and 300 kPa,
  the size of the interstices between the fibres is comprised between 0.1 and 50 µm$^2$, preferably between 0.5 and 10 µm$^2$, more preferentially between 1 and 2 µm$^2$,
  the crosslinked polymer comprises a stiffening compound, preferably selected from carbon nanotubes, at a concentration comprised between 0.00001 and 5%, preferably between 0.0001 and 1%, preferably between 0.0001 and 0.1%, preferably between 0.0002 and 0.08%, preferably between 0.00075 and 0.05%, expressed in weight percent of said fibres,
  the network emits a fluorescent light when it is subjected to a light energy, and
  the surface of the fibres of the network is coated with at least one protein of the extracellular medium, preferably laminin.

According to an even more particular aspect, a subject of the invention is a 3D network of PAN fibres characterized in that:
  the diameter of the fibres is comprised between 0.3 and 1 µm,
  the fibres comprise carbon nanotubes at a concentration comprised between 0.0002 and 0.08%, preferably comprised between 0.00075 and 0.05%, expressed in weight percent of said fibres,
  the stiffness of the network is characterized by an elastic modulus comprised between 0.1 and 1,000 kPa, preferably between 0.1 and 300 kPa, and
  the surface of the fibres is coated with laminin.

A second subject of the invention is a process for preparing a 3D network of fibres according to the invention, the process comprising the following steps:
  a) a step of synthesizing said network by electrospinning of a solution of acrylic-type polymer, the concentration of which is comprised between 5 and 25%, preferably between 8 and 12%, preferably 10%, expressed in weight percent of said polymer solution, to obtain a 3D network of fibres, and
  b) a step of heat treatment under oxidizing atmosphere and at a temperature comprised between 40° C. and 400° C., preferably between 200° C. and 300° C., preferably between 100° C. and 300° C., of the 3D network of fibres obtained during step a),
  said step a) of synthesis by electrospinning being characterized in that:
  the polymer solution is extruded from a needle, the displacement amplitude of which is comprised between 30 and 50 mm, preferably 40 mm, and the displacement rate of which is comprised between 2 and 10 mm/second, preferably 5 mm/second,
  the distance between the polymer source and the collecting electrode is comprised between 1 and 50 cm, preferably between 10 and 30 cm, more preferentially 15 cm, and the electrical field applied in the extrusion field is comprised between 16 and 24 kV, preferably 20 kV, and
  the flow rate of the polymer solution for supplying the syringe is comprised between 0.5 and 8.6 mL/h.

More particularly, in a process for preparing a 3D network of fibres according to the invention, said solution of acrylic-type polymer comprises polyacrylonitrile (PAN) and another acrylic-type polymer, the total concentration of polymer being comprised between 8 and 12%, preferably 10%.

More particularly, a second subject of the invention is a process for preparing a 3D network of fibres according to the invention, the process comprising the following steps:
  a) a step of synthesizing said network by electrospinning of a PAN solution the concentration of which is comprised between 8 and 12%, preferably 10%, expressed in weight percent of said PAN solution, to obtain a 3D network of fibres, and
  b) a step of heat treatment under oxidizing atmosphere and at a temperature comprised between 40° C. and 400° C., preferably between 200° C. and 300° C., of the 3D network of fibres obtained during step a),
  said step a) of synthesis by electrospinning being characterized in that:
  the PAN solution is extruded from a needle, the displacement amplitude of which is comprised between 30 and 50 mm, preferably 40 mm, and the displacement rate of which is comprised between 2 and 10 mm/second, preferably 5 mm/second,
  the distance between the polymer source and the collecting electrode is comprised between 1 and 50 cm, preferably between 10 and 30 cm, more preferentially 15 cm, and the electrical field applied in the extrusion field is comprised between 16 and 24 kV, preferably 20 kV, and
  the flow rate of the polymer solution for supplying the syringe is comprised between 0.5 and 8.6 mL/h.

According to this aspect, said solution is prepared from PAN, the degree of purity of which is greater than or equal to 90%, preferably greater than or equal to 92%, preferably greater than or equal to 95%, 96%, 97%, 98% or 99%. According to another aspect, said PAN is characterized by an average molecular weight (MW) of 150,000. PAN is marketed by different known suppliers. PAN marketed by Sigma-Aldrich® is particularly suitable for this aspect of the invention.

According to a first particular aspect, a process according to the invention is characterized in that the PAN solution is extruded onto a rotating collecting electrode, preferably a drum, with a diameter comprised between 12 and 18 cm, preferably 15 cm, the speed of rotation of said electrode being comprised between 1 and 100,000 g, preferably between 1 and 1,000 g and more preferentially 335 g. Implementation of such a process leads to a network comprising aligned fibres being obtained, said network of aligned fibres having a general orientation rather than fibres that are strictly parallel. According to another particular aspect, in a process according to the invention, the PAN solution is extruded onto a non-rotating flat collector, implementation of this other aspect of the process leads to synthesis of a 3D network comprising tangled fibres, in which the fibres do not have any general orientation.

According to another particular aspect, a process according to the invention is characterized in that the PAN solution does not comprise stiffening compound, such as nanoparticles, nanotubes, nanofibres or nanosheets. More particularly, a process according to the invention utilizes a PAN solution comprising carbon nanotubes, and in particular multi-walled carbon nanotubes (MWCTs). According to this particular aspect, the step of synthesis by electrospinning is characterized in that:

the electrical field applied in the extrusion field is comprised between 16 and 24 kV, preferably 20 kV, and the flow rate of the polymer solution for supplying the syringe is comprised between 0.5 and 8.6 mL/h, preferably between 2.1 and 2.7 mL/h, and preferably 2.4 mL/h.

According to another particular aspect, a process according to the invention is characterized in that the PAN solution comprises a stiffening compound, preferably selected from nanofillers, and more preferentially from: nanoparticles, nanotubes, nanofibres and nanosheets. More particularly, a process according to the invention utilizes a PAN solution comprising carbon nanotubes, and in particular multi-walled carbon nanotubes (MWCTs).

According to a more particular aspect, the fibres of said network comprise a stiffening compound, at a concentration comprised between 0.00001 and 5%, preferably between 0.00001 and 1%, preferably between 0.0001 and 0.1%, preferably between 0.002 and 0.08%, and preferably between 0.0075 and 0.05%, expressed in weight percent of the polymer solution before crosslinking.

According to another particular aspect, a process according to the invention comprises a step of electrospinning a polymer solution, said solution comprising a stiffening compound, preferably constituted by carbon nanotubes, and a dispersing agent, preferably a surfactant and more preferentially a non-ionic surfactant. The presence of said dispersing agent ensures good solubilization of said stiffening agent.

According to this particular aspect, a process according to the invention is characterized in that the PAN solution comprises a stiffening compound, selected from nanoparticles, nanotubes, nanofibres and nanosheets, preferably carbon nanotubes, and in particular multi-walled carbon nanotubes (MWCTs), and the step of synthesis by electrospinning is characterized in that:

the electrical field applied in the extrusion field is comprised between 16 and 24 kV, preferably 20 kV, and the flow rate of the polymer solution for supplying the syringe is comprised between 0.5 and 8.6 mL/h, preferably between 0.5 and 1.9 mL/h, and preferably between 0.8 and 1.5 mL/h.

More particularly, a process according to the invention is characterized in that the step b) of heat treatment applied to the 3D network comprises keeping said network under oxidizing atmosphere for at least 10 minutes, preferably between 10 and 300 minutes, preferably between 20 and 180 minutes, between 60 and 150 minutes, more preferentially for 120 minutes, at a temperature comprised between 40 and 400° C., preferably between 100 and 300° C., more preferentially at a temperature of 250° C. Said step of heat treatment under oxidizing atmosphere is preceded by an increase in temperature and followed by a decrease in temperature, according to the characteristics of the device used to apply said heat treatment.

During said heat treatment, the colour of the network passes from white to brown, reflecting the aromatization of the fibres and the crosslinking of the polymer.

More particularly according to this second aspect, a subject of the invention is a process comprising the following steps:

a) a step of synthesizing said network by electrospinning of a 10% PAN solution comprising 0.05% MWCT carbon nanotubes, said step a) being characterized in that:

the PAN solution is extruded from a needle the displacement amplitude of which is comprised between 30 and 50 mm and the displacement rate of which is comprised between 2 and 10 mm/second, the distance between the polymer source and the collecting electrode is comprised between 1 and 50 cm and the electrical field applied in the extrusion field is 20 kV, and the flow rate of the polymer solution for supplying the syringe is 2.4 mL/h. b) a step of heat treatment under oxidizing atmosphere and at a temperature comprised between 200° C. and 300° C., for 120 minutes, of the 3D network of fibres obtained during step a).

According to another particular aspect, a process according to the invention is characterized in that said heat treatment step is followed by the treatment of the surface of the fibres of the network, intended to functionalize said fibres, and in particular to contribute to the mimicking of the extracellular environment of the cells in contact with a 3D network according to the invention. According to a particular aspect of a process according to the invention, the surface treatment step comprises bringing the network into the presence of a solution of at least one protein of the extracellular matrix, in particular selected from: laminin, fibronectin, vitronectin, hyaluronic acid and collagen. This solution of at least one protein of the extracellular matrix is prepared in a suitable buffer and under suitable concentration conditions. For example, the laminin is prepared in phosphate-buffered saline (PBS) at a concentration comprised between 1 and 2 mg/ml, the network is then brought into contact with a laminin solution with a concentration comprised between 5 and 20 µg/ml.

In a process according to the invention, bringing the network into the presence of a solution of at least one protein of the extracellular matrix is optionally preceded by a prior treatment of the surface of the fibres of said network, intended to improve the quality of the functionalization of said network. Said prior treatment is implemented by any suitable method, known to a person skilled in the art, in particular by chemical deposition, implemented in liquid or gas phase. According to a preferred aspect, such a chemical deposition comprises bringing it into the presence of a poly-D-lysine solution at a concentration comprised between 5 and 50 µg/ml, in particular by immersion.

According to this particular aspect, a process according to the invention comprises treating the surface of the fibres of the 3D network by means of the following successive steps:
 prior treatment of the surface of the fibres,
 treatment of the surface leading to the functionalization of the fibres with at least one protein of the extracellular matrix selected from: fibronectin, vitronectin, hyaluronic acid and collagen, and preferably laminin.

According to a more particular aspect, a process according to the invention comprises treating the surface of the fibres of the 3D network by means of the following successive steps:
 prior treatment with a poly-D-lysine solution,
 treatment of the surface with a laminin solution.

A third subject of the invention is a device for cell support, comprising an infusible 3D network of crosslinked polymer fibres according to the invention or a network obtained by a process according to the invention.

A device for supporting cells according to the invention comprises an infusible 3D network of crosslinked polymer fibres according to the invention, more particularly an infusible 3D network of crosslinked acrylic-type polymer fibres according to the invention or a network obtained by a process according to the invention, in combination with any other element.

Such a device can in particular be constituted by said network as it is, or by said network arranged or inserted in any suitable support, such as for example a culture dish. By way of example, a device according to the invention can be constituted by a plate of the multi-well plate type of which at least one well comprises a 3D network of fibres according to the invention. According to a particular aspect, a subject of the invention is a device comprising one or more 3D networks according to the invention, identical or different, arranged or inserted within any appropriate support of the "multi-well plate" type.

A fourth subject of the invention is the use of a 3D network according to the invention, of a 3D network obtained by a process according to the invention or of a device comprising such a 3D network, as a cell support. Such a use comprises successively:
 bringing cells of interest into contact with a 3D network according to the invention, a 3D network obtained by a process according to the invention or a device comprising such a 3D network, under suitable conditions and for a suitable duration, and
 observing and optionally determining at least one parameter characterizing said cells and/or the biochemical analysis of said cells.

Said suitable conditions and duration are well known to a person skilled in the art specializing in cell culture, and relate in particular to the medium in which the cells are suspended, their concentration and their incubation temperature.

The parameters characterizing the cells are in particular selected from: the state of cell life or death, the cell number, the location of the cells at the surface of and/or within said network, the presence of isolated and/or grouped cells, the size and the shape of the cells, the characterization of the nucleus and the organelles. The means for observing said cells are in particular, but not exclusively, any type of microscopy, such as for example scanning electron microscopy, conventional fluorescence microscopy, confocal microscopy, multiphoton microscopy, epifluorescence microscopy, video microscopy and three-dimensional imaging.

The biochemical analysis of the cells comprises in particular, but not exclusively: qualitative and/or quantitative analysis of DNA, RNA, cellular proteins and metabolites, by any suitable means known to a person skilled in the art. Such means include in particular transcriptomic and proteomic studies.

According to a more particular aspect, a subject of the invention is the use of a 3D network according to the invention, of a 3D network obtained by a process according to the invention or of a device comprising such a 3D network, as a support for proliferating or cancerous cells. According to an even more particular aspect, a subject of the invention is the use of a 3D network according to the invention, of a 3D network obtained by a process according to the invention or of a device comprising such a 3D network, as a support for glioblastoma cells, more particularly invasive glioblastoma cells.

According to another more particular aspect, a subject of the invention is the use of a 3D network according to the invention, of a 3D network obtained by a process according to the invention or of a device comprising such a 3D network, for studying and characterizing the survival, proliferation, differentiation and/or migration of cells.

According to this aspect, said cells are in particular cancer cells, and more particularly glioblastoma cells.

Examples 1 to 4 and FIGS. 1 to 10 below illustrate the invention.

BRIEF DESCRIPTION OF THE DRAWINGS

FIG. 1A: scanning electron microscopy images (scale bar: 50 µm) of aligned (left-hand image) or non-aligned (right-hand image) PAN fibres; FIG. 1B: immunostaining image showing laminin deposits on the fibres (scale bar: 20 µm), FIG. 1C: 3D reconstruction from a "z-stack" corresponding to the acquisition of the image in FIG. 1B, the discontinuous deposits of laminin on the fibres are indicated by arrows (scale bar: 20 µm).

FIG. 2A: image showing the adherence and the penetration of the neurospheres in the 3D network (scale bar: 500 µm), at the moment of deposition of a neurosphere containing 5,000 cells; FIG. 2B: image showing the neurospheres of Gli4 cells 5 hours after deposition on the network of fibres (scale bar: 200 µm); FIG. 2C: image showing the neurospheres of Gli4 cells 6 days after deposition on the network of fibres (scale bar: 200 µm), FIG. 2D: side view of the distribution of the migratory Gli4 cells, moving away from the neurospheres and at a depth in the network of fibres (scale bar: 20 µm), FIG. 2E: immunostaining image showing the adhesion of the Gli4 cells to the fibres (scale bar: 10 µm), the arrows indicate the Gli4 cells; FIG. 2F: 3D reconstruction from a "z-stack" corresponding to the acquisition of the image of the Gli4 cells on the fibres (FIG. 2E).

FIGS. 3A and 3C: visualization of the Gli4 cells by scanning electron microscopy (scale bar: 500 µm), FIGS. 3B and 3D: visualization of the Gli4 cells after marking the actin cytoskeleton with phalloidin green (scale bar: 20 µm). In FIGS. 3A and 3B, the arrows indicate the lamellipodial extensions of the peripheral cells and the round cells situated at the centre of a group of cells which are migrating collectively, in the absence of laminin on the fibres. In FIGS. 3C and 3D, the arrows indicate the cells migrating individually, in the presence of laminin on the fibres.

FIGS. 5A and 5C: in the absence of laminin, 5B and 5D: in the presence of laminin, FIGS. 5A and 5B: non-aligned fibres, FIGS. 5C and 5D: aligned fibres.

EXAMPLES

Figures 1A, 1B, 1C:
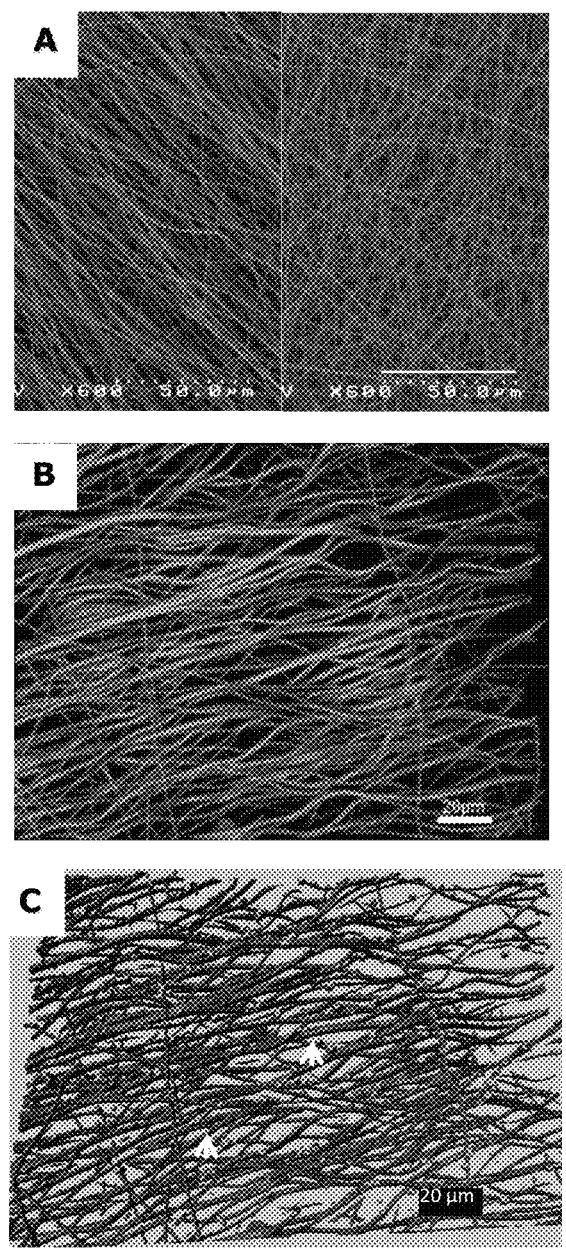
FIGS. 1A to 1C illustrate the physical characterization of a 3D network of fibres according to the invention, according to Example 1.

Example 1: Synthesis of a 3D Network of Polyacrylonitrile Fibres and Physical Characterization 1.1. Materials and Methods Synthesis of the 3D Network of PAN Fibres A 10% by weight solution of polyacrylonitrile (Sigma Aldrich) is prepared in dimethylformamide. For 10 g of 10% PAN solution: weighed out to a value of 1 g PAN for 9 g DMF, followed by heating to 75° C. under stirring until complete dissolution of the PAN in the DMF.

This solution is formed by electrospinning. The collector is a rotating collector 15 cm in diameter. A 20-kV electrical field is applied between the needle distributing the polymer and the collector.

3D network with aligned fibres: The needle is located at a distance of 15 cm from the rotating collector. The collector around which the fibres are wound has a speed of rotation of 2,000 rpm making it possible to obtain a network the fibres of which are aligned.

3D network with fibres called "tangled" fibres: The needle is located at a distance of 15 cm from a flat, non-rotating collector.

In both cases, the polymer is conveyed to the needle by a "syringe pump" with a pushing force of 2.4 ml/h in this case. During electrospinning, the needle performs displacements with an amplitude of 40 mm at a displacement rate of 5 mm/sec. The electrospinning lasts at least 20 minutes. The tissue of fibres then undergoes a heat treatment before being sterilized.

Heat Treatment of the 3D Network

The network obtained by electrospinning is heat-treated under air at a temperature of 250° C., with a heating rate of 120° C./hour, a plateau at 250° C. for 2 hours, the cooling rate is 300° C./h. During treatment, the colour of the network passes from white to brown, reflecting the aromatization of the fibres.

Before use, the network undergoes sterilization in 70° ethanol or in an autoclave.

Synthesis of a 3D Network of PAN Fibres and Carbon Nanotubes

During production of fibres containing multi-walled carbon nanotubes (Nanocyl™, 95% purity, product reference NC3101 or NC3151) and to increase the dispersion of the MWCTs in the PAN solution, the surfactant triton 100× is added at 2.5% of the final solution for 0.05% WT of MWCTs.

For a preparation of a 0.05% WT PAN solution, the following steps are carried out:
a) Preparation of 10 g of a 0.05% solution (weight percent) of MWCTs in 10% PAN:
   Weighed out to a value of 1 g PAN, 0.05 g MWCTs and 8.95 g DMF,
   Heating to 75° C. under stirring until complete dissolution of the PAN in the DMF,
   Sonication of the solution
b) Producing a 10% PAN solution according to section 1.1.1.
c) Mixing 1 g of 10% PAN +0.05% WT (weight percent) MWCT solution for 0.75 g Triton 100× and 8.25 g 10% PAN solution
d) Sonication of the mixed solution. The polymer solution is then treated by electrospinning, then the network obtained is heat-treated as indicated above.

By dilution with 10% PAN, a network constituted by PAN fibres and 0.0016% (weight percent) MWCTs is synthesized.

Coating the Surface of the Fibres with Laminin

For their functionalization by laminin, the culture dishes and the 3D network of biocompatible electrospun fibres are incubated overnight with 25 µg/m poly-D-lysine in borate buffer at 37%, then washed twice in sterile water and incubated with 5.2 µg/ml laminin in sterile water for 4 h at 37° C. It is washed twice with water.

Inclusion of the Network of Fibres in Wells

This inclusion can be carried out by cutting them out using a punch with a size corresponding to the size of the well intended to accommodate the fibres. The cut-out fibres are then deposited at the bottom of the well and ready for use.

It is also possible to position the cut-out fibres in inserts, of a size corresponding to the size of the wells, making it possible to make it easier for them to enter and be removed from the wells or making it possible to produce concentration gradients on both sides of the fibres.

1.2. Results

Characterization of a 3D Network of PAN Fibres

The diameter of the fibres, estimated at 0.68+/−0.28 µm, is similar to the diameter of the axons present in the corpus callosum, estimated at 0.64+/−0.42 µm (Liewald et al., 2014, *Biol. Cybern.* 108, 541-557). Depending on the electrospinning process implemented, the network of fibres generated comprises fibres aligned or organized randomly (FIG. 1A). The network of aligned fibres has a general orientation rather than fibres that are strictly parallel.

Evaluation of the mechanical properties is carried out by means of atomic force microscopy. The elasticity of the network constituted by PAN fibres with no carbon nanotubes added is characterized by an elastic modulus of 0.16 kPa. The experiments are carried out in contact mode on an Asylum MFP-3D device (Asylum Research, Santa Barbara, California, USA) mounted on an inverted microscope of the Olympus brand, using a silicon nitride triangular cantilever system (MLCTAUHW, Veeco) and with a stiffness constant of 10 pN/nm. The measurements are conducted by applying a maximum force of 1 nN. The stiffness is measured as an average value over all of the image recorded. For a network constituted by PAN fibres and 0.0016% (weight percent) MWCTs, the elasticity is characterized by an elastic modulus of 62 kPa.

For a network constituted by PAN fibres and 0.05% (weight percent) MWCTs, the elasticity is characterized by an elastic modulus of 250 kPa.

The interstices are such that the mesh of fibres is permissive but nevertheless constrains the cells to deform in order to enter into the matrix. The interstices are comprised between 0.5 µm$^2$ and 9 µm$^2$, which corresponds to a confinement location of the cells.

Fluorescence Properties

When the network is subjected to a light energy, the fibres appear as fluorescent (FIG. 1B). They are autofluorescent in the green (488 nm) and red (594 nm), and to a lesser extent in the blue (350 nm) and in the infrared (647 nm). The functionalization of the fibres with laminin makes it possible to modify the microenvironment.

Characterization of the Network Coated with Laminin

The laminin deposits are distributed discontinuously on the fibres (FIG. 1C).

Conclusion

The 3D network thus obtained is non-cytotoxic, and can constitute a 3D support for cells, allowing their proliferation, their migration and their differentiation.

Example 2: Characterization of the Migration of Glioblastoma Cells 2.1. Materials and Methods Culture of Glioblastoma Cells Obtaining and isolating glioblastoma cells (GBM) as well as the cultures are carried out using the protocol drawn up by Guichet et al. (Guichet et al., 2013, *Glia,* 61, 225-239), according to Dromard et al. (Dromard et al., 2008, *J. Neurosci. Res.* 86, 1916-1926) for non-adherent neurospheres. The Gli4 and GliT cells are primary glioblastoma cultures derived from two different patients. These GBM cells are cultivated under two different conditions in DMEM/F12 medium, supplemented with glucose, glutamine, insulin, N2 and ciproflaxin.

Under non-adherent conditions, called "proliferation" conditions, the culture dishes are pre-treated with poly-2 hydroxyethyl methacrylate (poly-HEMA, SIGMA), the medium is also supplemented with epidermal growth factor (EGF) and fibroblast growth factor (FGF), gentamicin, heparin, fungizone, fungin and B27. Under these conditions, the GBM cells form neurospheres (NSs) reminiscent of in vitro neural stem cells (NSCs), and express neural progenitors and stem cell markers (nestin, olig2, sox2, etc.), self-renew and propagate tumours in immunocompromised animals. After confluency, the NSs are mechanically dissociated using HBSS (without calcium or magnesium) and reseeded.

Under conditions called "differentiation" conditions, the DMEM/F12 contains foetal bovine serum (0.5%) without growth factor and without heparin. In this case, the GBM cells are cultivated adhering to a flat (2D) surface or on a 3D network prepared according to Example 1, without poly-HEMA.

Culture of Cells on the 3D Network

Before deposition of the cells, the 3D networks of biocompatible electrospun fibres (denoted "fibres"), prepared as described in Example 1, are sterilized in 70% alcohol, autoclaved and functionalized, or not, with poly-D-lysine/laminin, as described in Example 1. For the functionalization, the 2D culture dishes and the fibres are incubated overnight with 25 µg/ml poly-D-lysine in borate buffer at 37%, then washed twice in sterile water and incubated with 5.2 µg/ml laminin in sterile water for 4 h at 37° C. The dishes and the fibres are washed twice in sterile water and the neurospheres, or the dissociated cells, of Gli4 and GliT are seeded thereon. The cells are kept under culture conditions for 6 days at 37° C. and 5% $CO_2$.

In order to obtain neurospheres, 96-well Corning microplates are used (Corning 7007). The dissociated GBM neurospheres are cultivated under proliferation conditions, and seeded at 5,000 cells per well. The cells sediment and the NSs are harvested 24 hours after seeding.

Orthotopic Xenotransplantation of GBM

The Gli4 and GliT cells are enzymatically dissociated using 0.25% trypsin and resuspended in PBS at 0.5×10$^5$ cells per microliter. 3 microliters ($1.5 \times 10^5$ cells) are injected into the striatum (1 mm rostral, 2 mm lateral and 2.5 mm depth) of 6-week old female NMRI nude mice (Janvier laboratories) under anaesthesia with isoflurane. A Hamilton syringe connected to a pump is used to inject the cell suspension with a flow of 0.3 ml/min. At the end of the surgery, the remaining cells will be seeded to verify the cell viability. After 3 months, the animals are sacrificed under anaesthesia with pentobarbital and fixed with an intracardiac perfusion of PFA. The brains are recovered and post-fixed overnight in 4% PFA then immersed successively in 7%, 15% and 30% sucrase. Then, these brains are included in OCT (optimal cutting temperature), frozen in liquid nitrogen and preserved at −20° C. Coronal section of the brain 14 µm thick are produced in a cryostat.

Cryoselection of the 3D Networks

The 3D networks of fibres are included in an OCT compound. The thickness of the lateral sections is 14 µm.

Immunofluorescence and 3D Reconstruction

After 6 days of culture, the GSCs cultivated in NF or in dishes are fixed with 4% PFA. The 3D networks, the dishes and the sections of brain are blocked and permeabilized using 0.5% PBS-triton-5% horse serum. The primary antibodies are incubated overnight at 4° C. The secondary antibodies coupled to a fluorochrome are incubated for 2 h at ambient temperature at the dilution of 1/500. These antibodies are: N-cadherin (Abcam ab12221), calpain-2 (Abcam ab155666) and human nuclei (Millipore MAB 1281). The sections are mounted with Fluoromount and dried before observation. The actin cytoskeleton is highlighted with (green) phalloidin and the nuclei with Hoechst 33342. The images are taken with a Z-stack acquisition using Confocal 2 Zeiss LSM 5 Live DUO and Widefield 1-Zeiss Axio Imager Z1/Zen (equipped with an Apotome) microscopes. Imaris X64 8.1.2 software is used for reconstructing 3D images.

The quantifications are carried out with ZEN 2012 software.

The Gli4 cells cultivated on the fibres are fixed with glutaraldehyde 2.5% in PHEM buffer for one hour at ambient temperature then overnight at 4° C. The cells are then dehydrated with alcohol at 70%, 96% and 100% successively, then incubated in HMDS for drying.

Western Blot

The proteins are extracted from cultures on fibres in RIPA buffer (supplemented with phosphatase and protease inhibitors). 20 µg protein lysate are separated by SDS-PAGE and transferred onto PVDF membranes, which will be subsequently blocked with TBS-0.1% Tween-5% skimmed milk. The primary antibodies used are: Galectin-3 (abcam ab2785), Integrin β1 (Millipore AB 1952), Integrin α6 (abcam ab75737), FAK (abcam ab40794), phospho-FAK Y397 (abcam ab 80298), Talin1/2 (abcam ab11188), calpain-2 (abcam ab155666) and GAPDH as control (Millipore MAB374). Horseradish peroxidase coupled with secondary antibodies is incubated for 2 h at ambient temperature. The ChemiDoc XRS+ imager is used for detecting the chemiluminescence. The quantifications of pixels are carried out with Image Lab software.

Characterization of the Cell Migration

The direction and the distance of migration of the Gli4 cells are analysed on aligned or non-aligned fibres, coated or not coated with laminin. At T=0, neurospheres having 5,000 cells are seeded. The number of cells per migration distance is quantified with AXIO-IMAJEUR software. Essentially, concentric arcs are defined from the centre of the sphere at regular intervals and the number of cells present between 2 successive arcs is counted, thus defining a number of cells per migration distance interval. The migration arcs are comprised between 200 and 2,000 µm from the edge of the neurosphere. This space is chosen to exclude migration associated with the expansion of NS growth. This test is carried out in 2D and 3D.

Statistical Analysis

At least 3 replicates are produced per experiment. The values are expressed as an average +/−SD. The statistical tests are carried out with GraphPad software.

2.2. Results

Figures 2A, 2B, 2C, 2D, 2E, 2F:
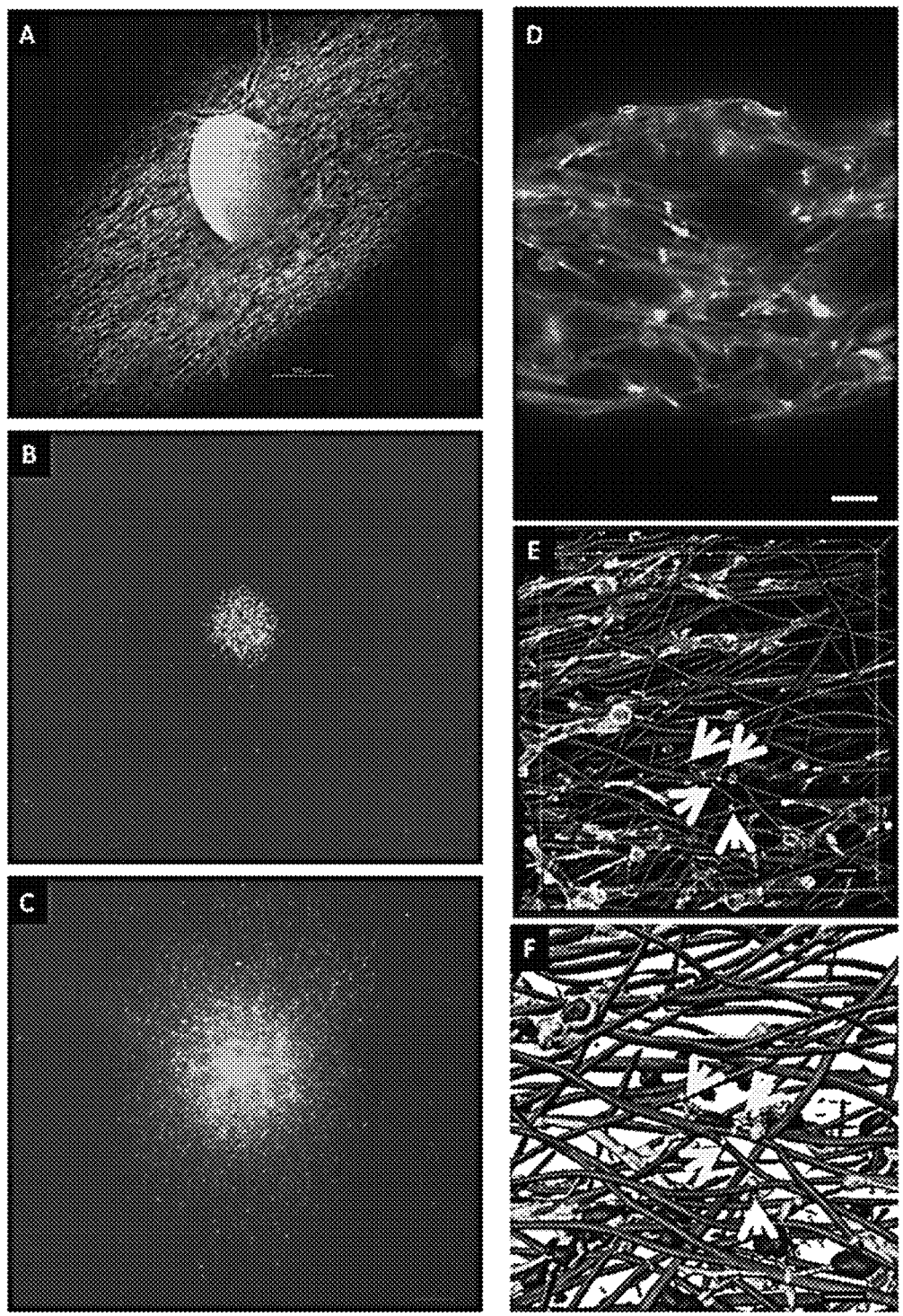
FIGS. 2A to 2F illustrate the adherence and the penetration of the neurospheres (NSs) within the network of fibres, according to Example 2.
Figures 3A, 3B, 3C, 3D:
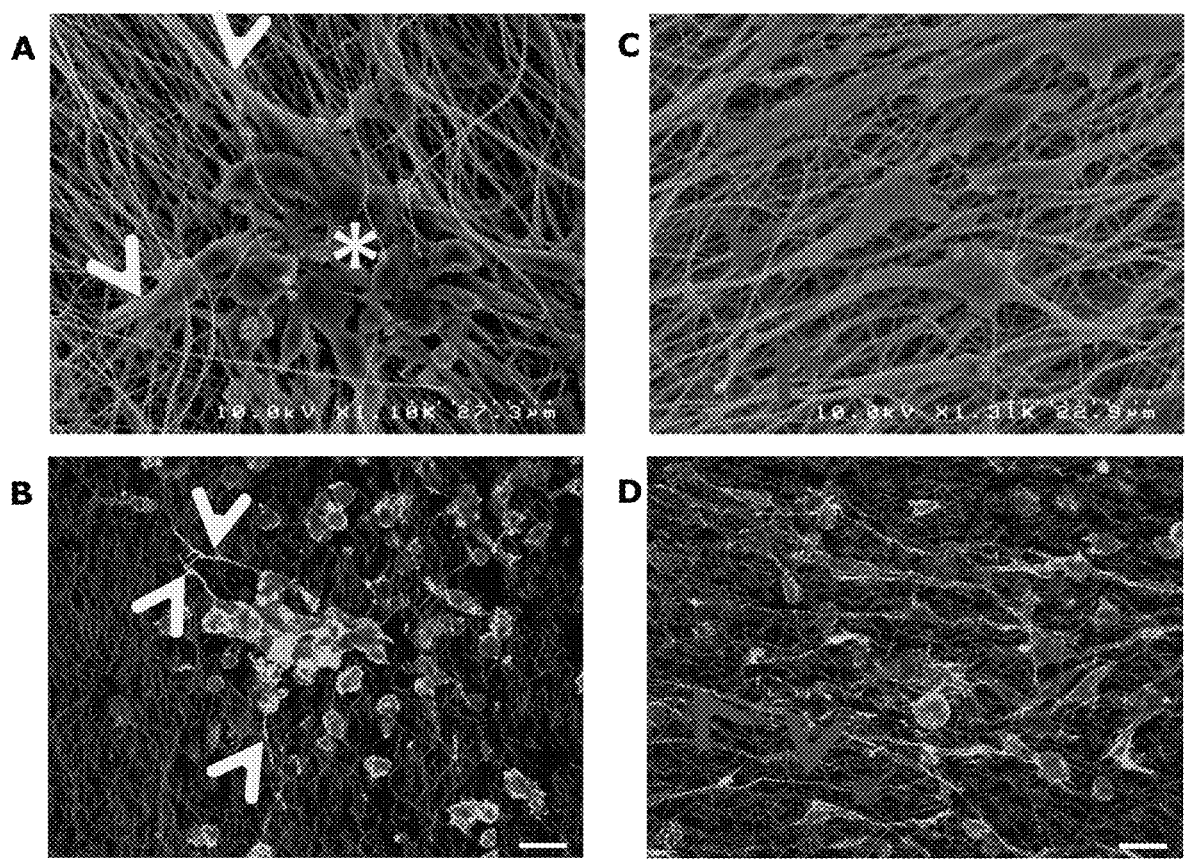
FIGS. 3A to 3D illustrate the individual or collective migration of cells deposited on a 3D network of fibres, according to Example 2, after 6 days of culture under differentiation conditions, in the absence (FIGS. 3A and 3B) or in the presence (FIGS. 3C and 3D) of laminin.

The aligned fibres constitute a 3D environment for the adhesion and the migration of glioma cells The network of fibres makes it possible to better understand, characterize and target the cells migrating in the corpus callosum. When they are deposited on a 2D surface and cultivated in the absence of growth factors and in the presence of serum (differentiation medium), the neurospheres (NSs) adhere to the support and the Gli4 cells differentiate themselves and migrate by moving away from the NSs (Guichet et al., "*Cell death and neuronal differentiation of glioblastoma stem-like cells induced by neurogenic transcription factors*", Glia. February; 61(2):225-39, 2013). When they are seeded on the 3D network of fibres and cultivated in the differentiation medium, the Gli4 NSs adhere to the surface and penetrate into the network of fibres (FIG. 2A). The Gli4 cells proliferate and migrate by moving away from the NSs (FIGS. 2A-2C). Analysis of the distribution of the Gli4 cells within the network of fibres shows that the cells migrate deeply inside the network (FIG. 2D). In this environment, the Gli4 cells form cell extensions in different directions in order to attach to several fibres, in a three-dimensional manner (FIGS. 2E and 2F). The Gli4 cells have a diameter of approximately 40 times that of the fibres (20 µm versus approximately 0.5 µm) and surround the fibres in order to adhere and migrate (FIGS. 2E and 2F, arrows). This surrounding makes it possible for the Gli4 cells to interact in a ventral, lateral and dorsal manner within the network. In addition, the heterogenous interstices between the fibres are distributed between 0.1 and 10 µm², with a maximum distribution between 1 and 2 µm². These spaces force the cells to deform in order to penetrate into the network of fibres (FIG. 2D), which is reminiscent of the natural cellular confinement observed in vivo (Friedl and Alexander "*Cancer invasion and the microenvironment: plasticity and reciprocity*", Cell, 147, 992-1009, 2011). These results show that the PAN fibres are permissive for the adhesion and the migration of the glioblastoma cells in a 3D microenvironment.

Dynamics of the cellular adhesion to the proteins of the extracellular matrix and the focal adhesion of the Gli4 cells with regard to flat (2D) conventional surfaces and aligned (3D) fibres In order to compare the interactions between the Gli4 cells and the extracellular medium (ECM) and their focal adhesion (AF) on the flat surfaces and in the 3D network of fibres, functionalized or not with laminin (+or −LN), the expression of integrin β1, integrin α6 and galectin-3 was analysed. Between the dishes coated with laminin (PS+LN) and the fibres coated with laminin (NF+LN), the level of expression of galectin-3 and integrin β1 was increased by 6 and 2.6 times, respectively, and the level of integrin α6 was reduced by 2.5 times. Between the flat surfaces and the networks not coated with laminin, no difference between the levels of expression of integrins β1 and α6 is observed. By immunofluorescence, integrin β1 is located on the membrane of the Gli4 cells migrating on the 3D network coated with laminin, when it is distributed in the cytoplasm and around the nucleus in the Gli4 cells deposited on the flat surfaces coated with laminin. In addition, on the networks of fibres coated with laminin, the staining of the integrin β1 is located on the points of attachment with the fibres. In addition, the phosphorylation of the focal adhesion kinase (FAK), a major actor in the transduction of the integrin-mediated signal, increases when the flat surfaces or the 3D network are coated with laminin.

The expression of talin ½, vinculin and calpain-2 in the Gli4 cells on the PS+LN and NF+LN supports was measured. The intact and cleaved forms were detected in the Gli4 cells on the flat surfaces with and without laminin, with the highest rate of cleaving of the talin on the PS+LN support. Conversely, talin ½ is not cleaved in the Gli4 cells on fibres, with or without laminin. The level of expression of vinculin does not vary under different conditions. The expression of calpain-2 is reduced by a factor of 2 for the Gli4 cells deposited on the fibres coated with laminin compared with the flat surfaces coated with laminin.

These results show that the adhesion mediated by integrin β1 and galectin-3 to ECM is increased on the electrospun fibres. The dynamics of the focal adhesion are regulated by the expression of calpain-2 and the cleaving of the talin differs between the flat surface and the 3D network.

Adherence of the GliT cells and their interaction with the cells of the extracellular matrix are not improved on the fibres The GliT cells are another primary line of neuroblastoma cells, less invasive than Gli4 in vivo. GliT and Gli4 differ in the expression of numerous proteins linked with the extracellular matrix, in particular the different expression of galectin-3, integrin β1 and integrin α6, in the different systems studied (flat surface or neurofibres, with or without laminin). Adhesion of the GliT cells via galectin-3, integrin β1 and integrin α6 is not improved in the presence of the network of fibres.

Integrin β1 and galectin-3 are overexpressed in Gli4 cells in the corpus callosum while calpain-2 is underexpressed in invasive Gli4 and GliT cells in vivo The results obtained indicate that the Gli4 cells are more invasive than the GliT cells, and that the expression of integrin β1 and galectin-3 in the Gli4 cells is dependent on the cerebral microenvironment and that the expression of calpain-2 seems to be inversely correlated with the invasive potential of the invasive glioblastoma cells (GICs) in vivo.

The Gli4 cells migrate individually or collectively in the presence or in the absence of laminin on aligned PAN fibres.

As observed using fluorescence microscopy and 3D image reconstruction by electron microscopy (FIGS. 3A to 3D), when they are seeded on a 3D network of fibres not coated with laminin, the Gli4 cells migrate collectively forming clusters composed of cells that are strongly combined with one another. Conversely, in the presence of a network of fibres coated with laminin, the Gli4 cells separate from one another and migrate individually. The cells thus adopt two different migration modes, collective mode or individual mode, depending on the functionalization of the fibres. In addition, on the fibres "without laminin", the staining of the actin of the cytoskeleton with phalloidin shows that the majority of the cells are round, within the clusters the actin cytoskeleton is continuous between the cells, at the centre of the cell mass the cells are round while on the outside of the cluster they are bipolar and have a lamellipodium. Conversely, on the network of fibres coated with laminin, the Gli4 cells are individual, bipolar, asymmetrical and each has a lamellipodium on the front face. In addition, the cells express N-cadherin on their membrane.

Moreover, the number of collective migration events by neurospheres was quantified, on the 3D network functionalized with laminin or not. To this end, neurospheres of the same size and containing the same number of cells were seeded on the two networks. A significant reduction (****p<0.0001) in the number of collective migrations by neurospheres is observed after the functionalization of the fibres with laminin. The number of units of collective migration per neurosphere decreases from 80 to 20 when the fibres are functionalized.

The Gli4 cells respond to a topoinduction signal resulting from the orientation and organization of the biocompatible electrospun fibres.

Figure 4:
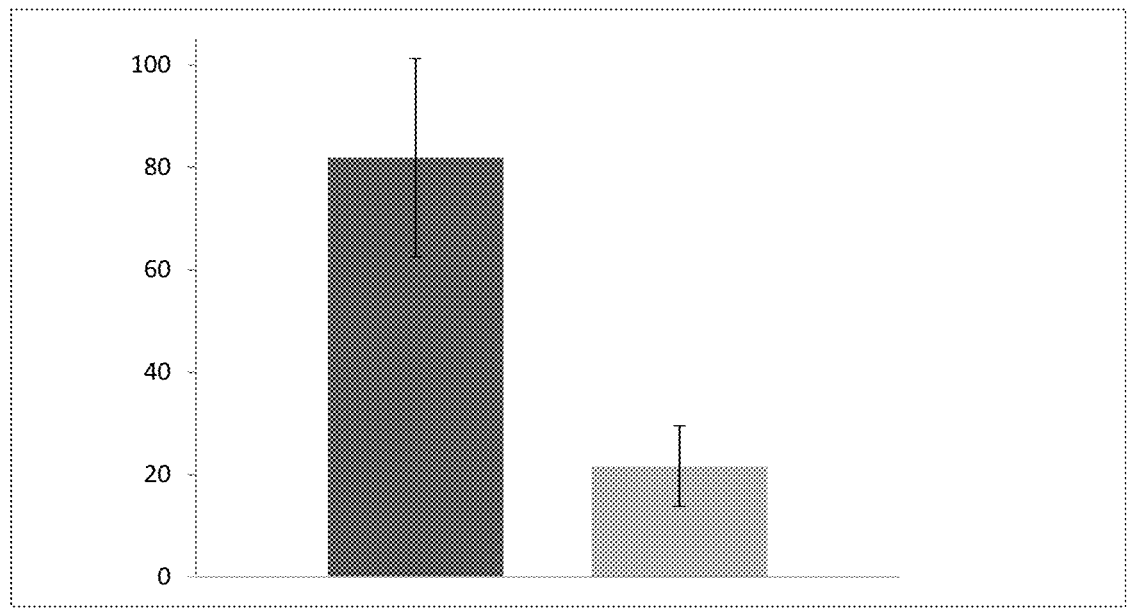
FIG. 4 illustrates the number of collective migrations (y-axis) quantified in the presence (left-hand histogram) or in the absence (right-hand histogram) of laminin on the aligned fibres, the clusters formed by at least 2 cells and physically separated from the neurospheres are considered as a collective migration, the results are representative of at least 3 different experiments, ****$p<0.0001$ (Student's t-test).

The direction of the migration of the Gli4 cells on the aligned fibres (AF) or non-aligned fibres (N-AF), functionalized by laminin or not, is compared. The results show that the presence of laminin increases the number of cells migrating outside the NSs, on aligned and non-aligned fibres. On the non-aligned fibres, the Gli4 cells migrate by moving away from the neurospheres in all directions, in the absence or in the presence of laminin. On the aligned fibres, the Gli4 cells migrate predominantly in the direction of the fibres, rather than in the perpendicular direction, and this effect is observed mainly in the presence of laminin. The number of migratory cells, as a function of the distance of migration on the fibres was quantified. The length of the migration region was delimited between the edge of the neurospheres and a distance of 2 mm in the direction of migration. The results show a significant increase in the number of migratory cells on the non-aligned fibres in the presence of laminin (right-hand histogram), in comparison with the non-aligned fibres without laminin (left-hand histogram) (FIG. 4). The addition of laminin increases the number of Gli4 cells migrating in a direction parallel to the aligned fibres, and in a perpendicular direction. In a direction parallel to the fibres and in the presence of laminin, the number of Gli4 cells increases significantly at a distance between 200 and 800 μm from the edge of the NSs, by comparison with the non-functionalized fibres. The same result is observed in the direction perpendicular to the aligned fibres, in which the number of cells also increases significantly at a distance between 200 and 600 μm from the edge of the NSs in the presence of laminin.

Conversely, no significant difference is observed in the number of migratory cells near to the edge of the NSs (from 0 to 200 μm), in parallel with and perpendicular to the fibres, in the presence and in the absence of laminin. The presence of cells adjacent to the NSs results from proliferation more than migration. A significant increase in the number of cells migrating in a direction parallel to the aligned fibres is observed compared with the perpendicular direction, in the absence and in the presence of laminin. In the model described, it is therefore not necessary for the fibres to be aligned in order to create interstitial spaces that are permissive for cell infiltration.

Together, these results show that the presence of laminin increases the migration of Gli4 cells on the aligned and non-aligned fibres. In addition, the orientation of the fibres dictates the direction of the migration of the Gli4 cells. On the non-oriented fibres the Gli4 cells migrate in all directions, while on the aligned fibres they migrate more in a direction parallel to the fibres than in a perpendicular direction.

In conclusion, the 3D matrix of electrospun fibres allows the adhesion of glioblastoma cells and their migration in a 3D microenvironment. This model shows the importance of cell-cell adhesion via N-cadherin in the collective migration process and the role of laminin in the accelerated migration of glioblastoma cells. This matrix of fibres represents an important tool, in particular for studying the role of the extra-cellular matrix in the migration of glioblastoma cells.

Example 3: Synthesis of 3D Networks of Acrylic-Type Polymer FIBRES AND PHYSICAL CHARACTERIZATION 3.1. Materials and Methods 3.1.1. 3D Network of Aligned Fibres of 5% PMMA, 5% PAN Polymer A 5% by weight solution of polyacrylonitrile (Sigma Aldrich) and 5% poly(methyl methacrylate) (PMMA, Sigma-Aldrich) is prepared in dimethylformamide. For 10 g polymer solution: weighed out to a value of 0.5 g PAN and 0.5 g PMMA for 9 g DMF, followed by heating to 75° C. under stirring until complete dissolution of the polymers in the DMF.

This solution is formed by electrospinning. The collector is a rotating collector 15 cm in diameter. A 20-kV electrical field is applied between the needle distributing the polymer and the collector. The needle is located at a distance of 15 cm from the rotating collector. The collector around which the fibres are wound has a speed of rotation of 2,000 rpm, making it possible to obtain a network the fibres of which are aligned. The polymer is conveyed to the needle by a "syringe pump" with a pushing force of 3.4 ml/h in this case. During electrospinning, the needle performs displacements with an amplitude of 40 mm at a displacement rate of 5 mm/sec. The electrospinning lasts at least 20 minutes. The tissue of fibres then undergoes a heat treatment before being sterilized.

The network obtained by electrospinning is heat-treated under air at a temperature of 110° C., with a heating rate of 120° C./hour, a plateau at 110° C. for 1 hour, the cooling rate is 300° C./h. During treatment, the colour of the network passes from white to brown, reflecting the aromatization of the fibres. Before use, the network undergoes sterilization in 70° ethanol or in an autoclave.

3.1.2. 3D Network of Fibres of 5% PMMA, 10% PAN Polymer

A 10% by weight solution of polyacrylonitrile (Sigma Aldrich) and 5% poly(methyl methacrylate) (PMMA, Sigma-Aldrich) is prepared in dimethylformamide. For 10 g polymer solution: weighed out to a value of 1.0 g PAN and 0.5 g PMMA for 8.5 g DMF, followed by heating to 75° C. under stirring until complete dissolution of the polymers in the DMF.

This solution is formed by electrospinning. The collector is a rotating collector 15 cm in diameter. A 20-kV electrical field is applied between the needle distributing the polymer and the collector. The needle is located at a distance of 15 cm from the rotating collector. The collector around which the fibres are wound has a speed of rotation of 2,000 rpm, making it possible to obtain a network the fibres of which are aligned. The polymer is conveyed to the needle by a "syringe pump" with a pushing force of 2.4 ml/h in this case. During electrospinning, the needle performs displacements with an amplitude of 40 mm at a displacement rate of 5 mm/sec. The electrospinning lasts at least 20 minutes. The tissue of fibres then undergoes a heat treatment before being sterilized.

The network obtained by electrospinning is heat-treated under air at a temperature of 110° C., with a heating rate of 120° C./hour, a plateau at 110° C. for 1 hour, the cooling rate is 300° C./h. During treatment, the colour of the network passes from white to brown, reflecting the aromatization of the fibres.

Before use, the network undergoes sterilization in 70° ethanol or in an autoclave.

3.1.3. 3D Network of 20% PMMA Polymer Fibres,+DMF +THF

A 20% by weight solution of poly(methyl methacrylate) (PMMA, Sigma-Aldrich) is prepared in a mixture of dimethylformamide and tetrahydrofuran (THF). For 10 g polymer solution: weighed out to a value of 2.0 g PMMA for 4 g DMF and 4 g THF, followed by stirring until complete dissolution of the polymers in the solvent. This solution is formed by electrospinning. The collector is a rotating collector 15 cm in diameter. A 20-kV electrical field is applied between the needle distributing the polymer and the collector. The needle is located at a distance of 15 cm from the rotating collector. The collector around which the fibres are wound has a speed of rotation of 2,000 rpm, making it possible to obtain a network the fibres of which are aligned. The polymer is conveyed to the needle by a "syringe pump" with a pushing force of 3.8 ml/h in this case. During electrospinning, the needle performs displacements with an amplitude of 40 mm at a displacement rate of 5 mm/sec. The electrospinning lasts at least 20 minutes. The tissue of fibres then undergoes a heat treatment before being sterilized.

The network obtained by electrospinning is heat-treated under air at a temperature of 110° C., with a heating rate of 120° C./hour, a plateau at 110° C. for 1 hour, the cooling rate is 300° C./h. During treatment, the colour of the network passes from white to brown, reflecting the aromatization of the fibres.

Before use, the network undergoes sterilization in 70° ethanol or in the autoclave.

3.2. Results

Characterization of the 3D Networks of Polymer Fibres

Figures 5A, 5B, 5C, 5D:
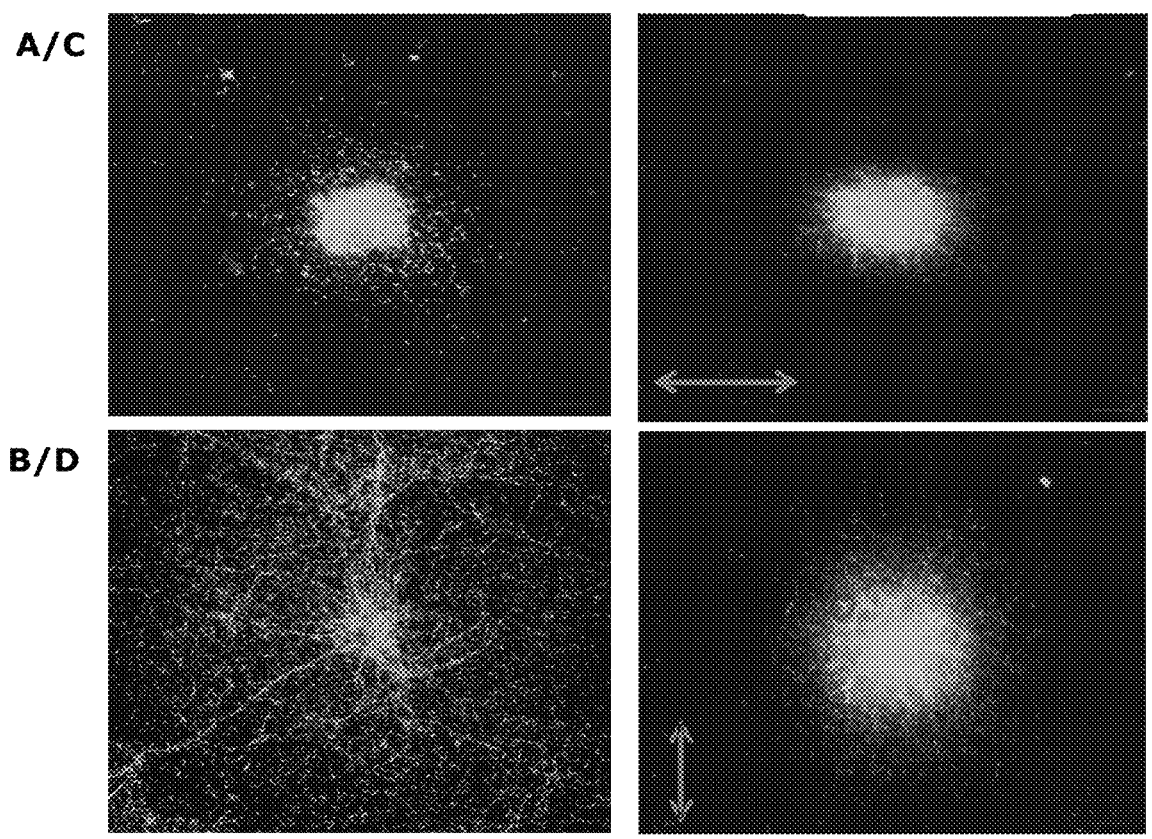
FIGS. 5A to 5D illustrate the direction of the migration of the cells on aligned or non-aligned fibres, according to Example 2, after 6 days of culture under differentiation conditions on a 3D network of fibres: the actin skeleton was stained with phalloidin and the nucleus with Hoechst 3342 stain (scale bar 200 μm), the direction of the fibres is indicated by the arrows.
Figure 6:
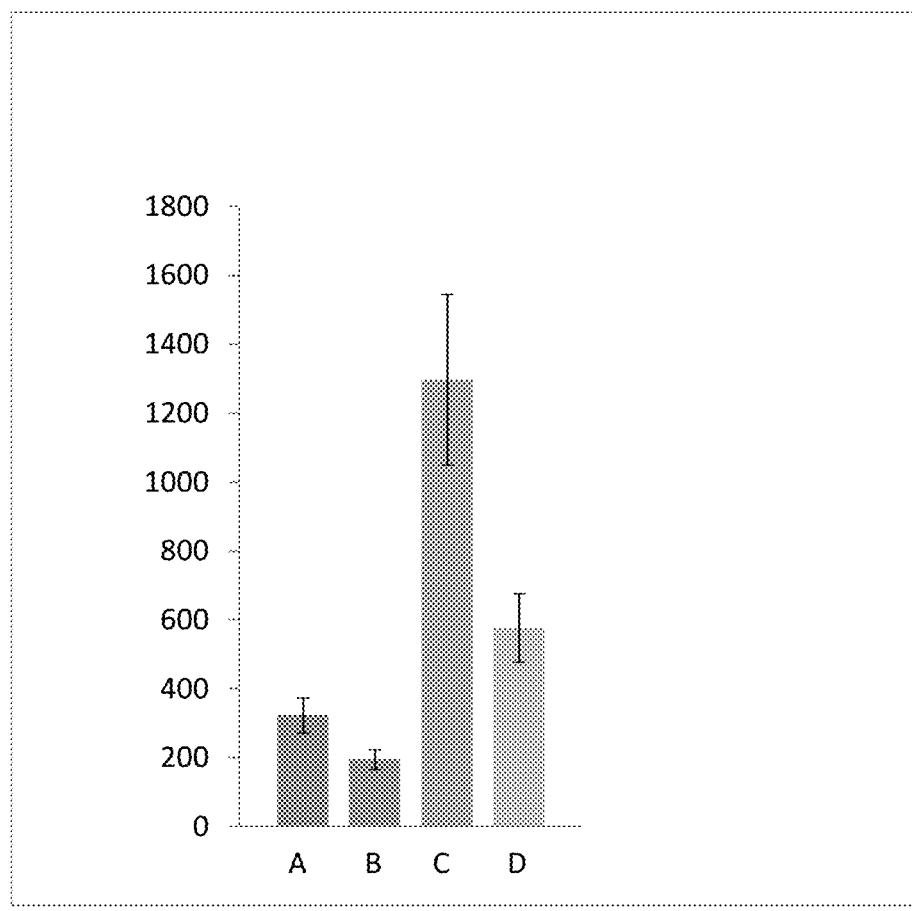
FIG. 6 represents the quantification (y-axis) of the total number of Gli4 cells migrating in a parallel (bars A and C) or perpendicular (bars B and D) direction of the aligned fibres, in the absence (bars A and B) or presence (bars C and D) of laminin. The number of cells is counted at a distance comprised between 200 μm and 2,000 μm of the outer edge of the neurospheres. This field was chosen to exclude migration due to expansive growth of the cells near to the neurospheres. Between bars A and B: *$p<0.1$, between bars C and D: **$p<0.01$ (Student's t-test). All the results are representative of two independent experiments.
Figures 7A, 7B, 7C:
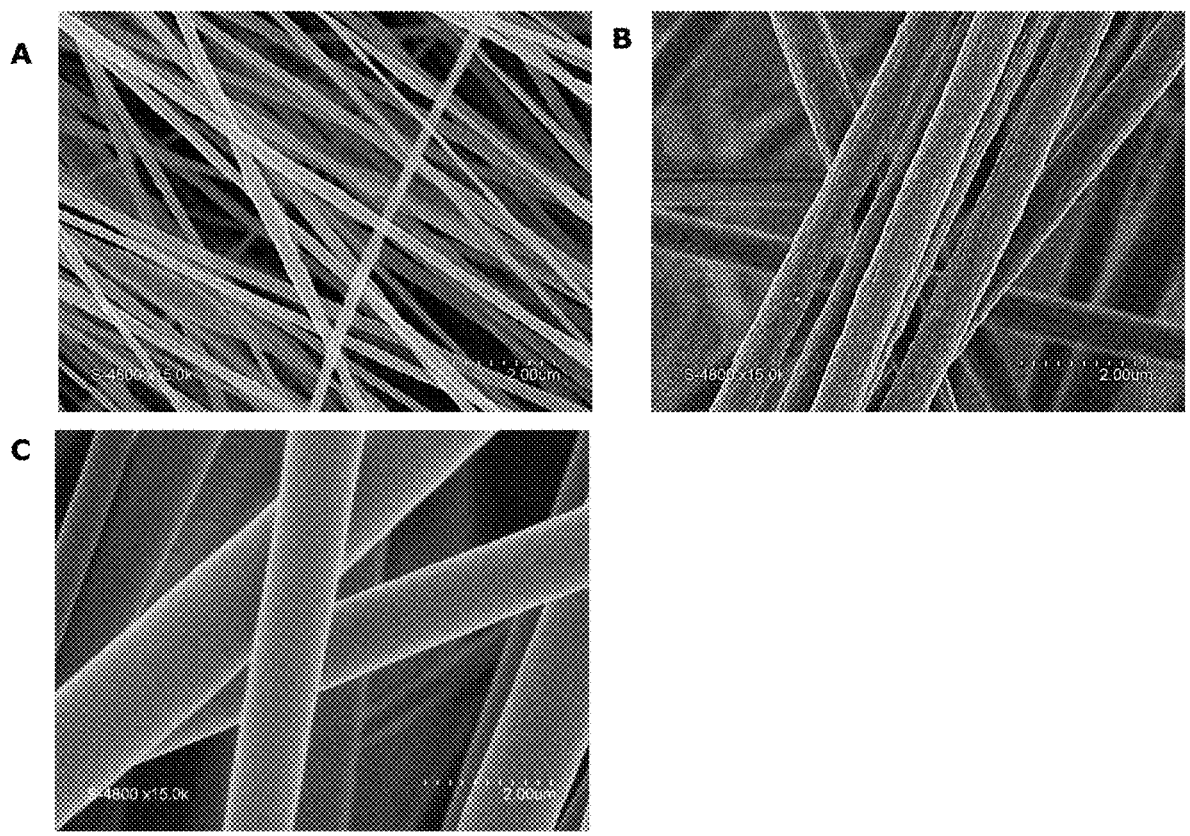
FIGS. 7A to 7C represent scanning electron microscopy images (scale bar: 200 μm) of crosslinked polymer fibres, said polymer is obtained by crosslinking of 5% PMMA+5% PAN (FIG. 7A), 5% PMMA+10% PAN (FIG. 7B) or 20% PMMA (FIG. 7C) solutions.

FIGS. 7A to 7C represent the 3D networks according to the invention obtained by crosslinking of the polymer solutions comprising respectively:
 5% PMMA, 5% PAN in DMF: FIG. 7A
 5% PMMA, 10% PAN in DMF: FIG. 7B
 20% PMMA, in DMF+THF: FIG. 7C The scanning electron microscopy images show that the average diameter of the fibres is 300 nm in the case of the "5% PMMA, 5% PAN" mixture, 600 nm in the case of the "5% PMMA, 10% PAN" mixture and 1.2 μm in the case of "20% PMMA".

Example 4: Characterization of the Viability of Glioblastoma Cells

4.1. Materials and Methods

Culture of Gli4 Glioblastoma Cells

Culture of Cells on the 3D Network

Before deposition of the cells, the 3D networks of biocompatible electrospun fibres (denoted "fibres"), prepared as described in Example 3, are sterilized in autoclaved 70% alcohol. The dishes and the fibres are washed twice in sterile water.

In order to obtain neurospheres, 96-well Corning microplates are used (Corning 7007). The dissociated Gli4 neurospheres are cultivated under proliferation conditions, and seeded at 5,000 cells per well. The cells sediment and the NSs are harvested 24 hours after seeding.

4.2. Results

Figure 8:
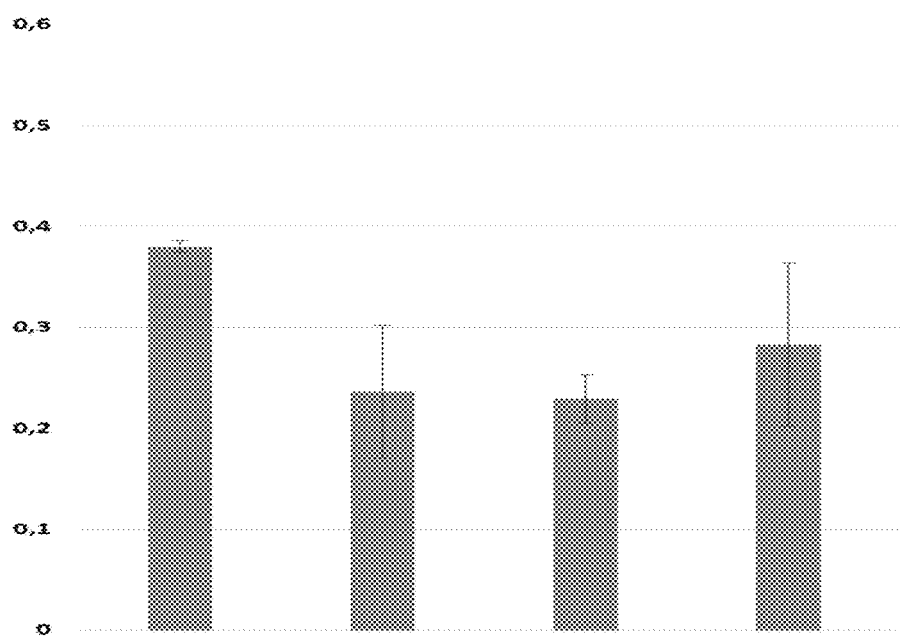
FIG. 8 (MTT assay) is a histogram illustrating on the y-axis the absorbance of formazan produced by reduction of MTT tetrazolium salt (3-(4,5-dimethylthiazol-2-yl)-2,5-diphenyl tetrazolium bromide) by living and metabolically active cells on the polymer fibres, and on the x-axis, from left to right, 10% PAN; 5% PMMA+5% PAN; 5% PMMA+10% PAN and 20% PMMA.
Figures 9A, 9B, 9C:
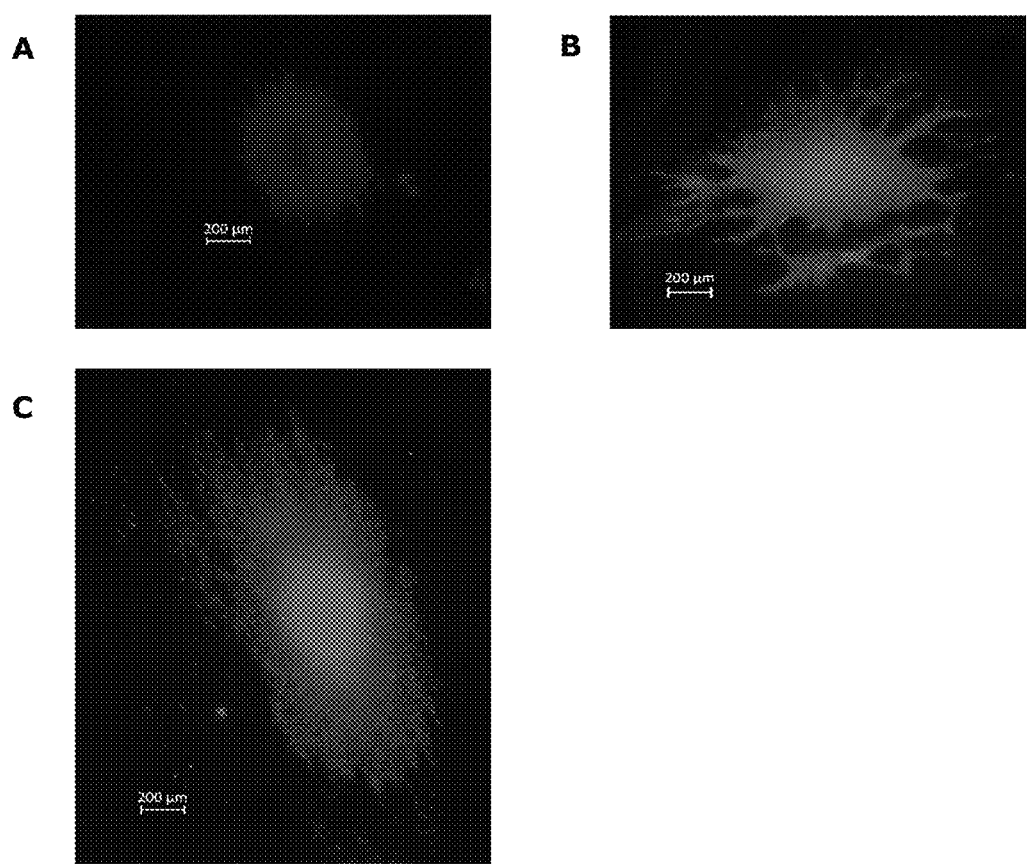
FIGS. 9A to 9C represent the direction of the migration of Gli4 cells on the 10% PAN (FIG. 9A), 5% PMMA+5% PAN (FIG. 9B) or 20% PMMA (FIG. 9C) fibres after 5 days of culture under differentiation conditions on a 3D network of fibres: the actin skeleton was stained with phalloidin and the nucleus with Hoechst 3342 stain.
Figure 10:
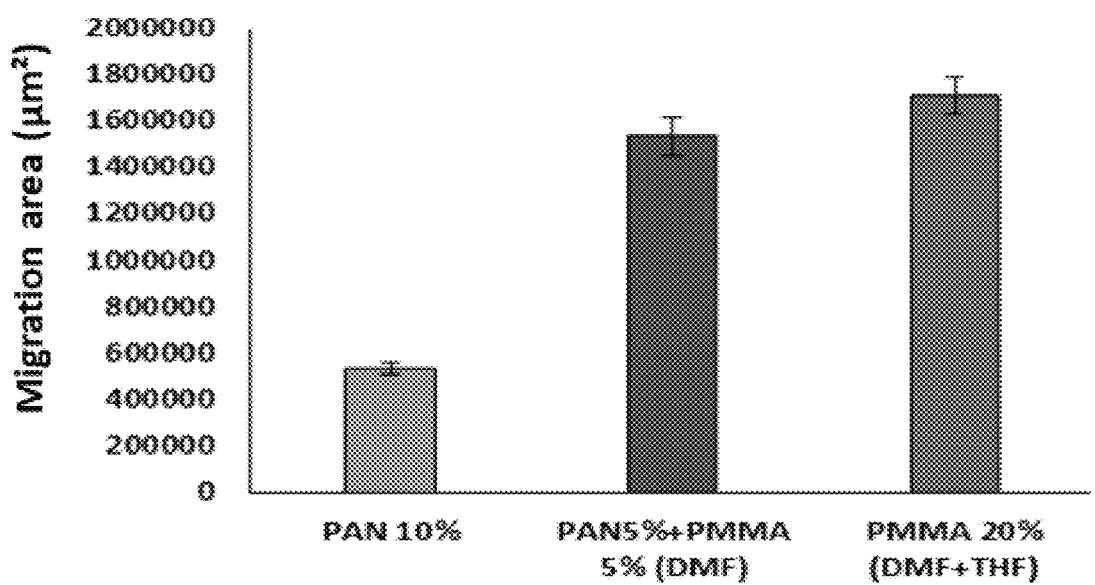
FIG. 10 represents a histogram indicating, on the y-axis, the surface area of the migration area (in pmt) of the Gli4 cells deposited on the polymer fibres, and on the x-axis, from left to right, of 10% PAN, 5% PAN+5% PMMA, or 20% PMMA.

FIG. 8 (MTT assay) is a histogram illustrating on the y-axis the absorbance of formazan produced by reduction of MTT tetrazolium salt (3-(4,5-dimethylthiazol-2-yl)-2,5-diphenyl tetrazolium bromide) by living and metabolically active cells on the polymer fibres, and on the x-axis, from left to right, 10% PAN; 5% PMMA+5% PAN; 5% PMMA+10% PAN and 20% PMMA. This MTT assay, well known to a person skilled in the art, shows that the 3D network constituted by fibres derived from acrylics or obtained from a mixture of acrylic-type polymers do not show cytotoxicity. This test was carried out on 30,000 dissociated Gli4 cells deposited on each network of fibres. The incubation time is 5 days in differentiation medium.

Example 5: Characterization of the Migration of Glioblastoma CELLS

5.1. Materials and Methods

Before deposition of the cells, the 3D networks of biocompatible electrospun fibres (denoted "fibres"), prepared as described in Example 3, are sterilized in autoclaved 70% alcohol. The dishes and the fibres are washed twice in sterile water.

In order to obtain neurospheres, 96-well Corning microplates are used (Corning 7007). 7500 Gli4 cells are deposited in each well and cultivated under proliferation conditions so as to form Gli4 neurospheres of the same size. The NSs are harvested 48 hours after seeding and deposited on the different fibres. The neurospheres are left to migrate for 5 days in a differentiation medium before fixing and staining as described in Example 1.

5.2. Results

The fluorescence microscopy images of Gli4 in neurospheres of the same size (7500 cells) seeded on the fibres derived from acrylic or obtained from a mixture of acrylic-type polymers show a permissivity of said networks for cell migration as well as an adherence of the cells. The Gli4 migrate in parallel with the preferred orientation of the network of fibres. The actin cytoskeleton of the Gli4 is marked with phalloidin and the nucleus is marked with Hoechst. The migration areas are then calculated using Zen software, by subtracting the initial area of the neurosphere, making it possible to evaluate the amplitude of the migration on the fibres. The results (FIGS. 9A to 9C, FIG. 10) show the influence of the physical and chemical characteristics of the fibres on the migration kinetics.

The invention claimed is:

1. An infusible three-dimensional network of crosslinked acrylic-type polymer fibers, wherein:
   the diameter of said fibers is comprised between 0.1 and 1.5 µm;
   the size of the interstices between said fibers is comprised between 0.1 and 50 µm$^2$; and
   the stiffness of said network includes an elastic modulus comprised between 0.01 and 10,000 kPa.

2. The three-dimensional network according to claim 1, wherein:
   the polymer of said fibers is obtained by thermal crosslinking of polyacrylonitrile (PAN), and
   the stiffness of the network includes an elastic modulus between 0.01 and 10,000 kPa.

3. The three-dimensional network according to claim 2, wherein:
   the polymer of said fibers is obtained by thermal crosslinking of PAN;
   said crosslinked polymer comprises nanofillers, at a concentration comprised between 0.00001 and 5% said percentage being expressed in weight percent of the polymer solution before crosslinking;
   the stiffness of the network includes an elastic modulus between 0.1 and 1,000 kPa; and
   the surface of the fibers is coated with laminin.

4. A process for preparing a three-dimensional network of crosslinked acrylic-type polymer fibers according to claim 3, said process comprising the following successive steps:
   a) a step of synthesizing said network by electrospinning of a PAN solution the concentration of which is comprised between 8 and 12%, expressed in weight percent of said PAN solution, in order to obtain a three-dimensional network of fibers; and
   b) a step of heat treatment under oxidizing atmosphere and at a temperature comprised between 40° C. and 400° C. of the three-dimensional network of fibers obtained during step a);
   wherein in said step of synthesis by electrospinning:
   the PAN solution is extruded from a needle the displacement amplitude of which is comprised between 30 and 50 mm, and the displacement rate of which is comprised between 2 and 10 mm/second;
   the distance between the polymer source and the collecting electrode is comprised between 1 and 50 cm, and the electrical field applied in the extrusion field is comprised between 16 and 24 kV; and
   the flow rate of the polymer solution during supply of the syringe is comprised between 0.5 and 8.6 mL/h.

5. The process according to claim 4, wherein the PAN solution is extruded onto a rotating collecting electrode, with a diameter comprised between 12 and 18 cm, the speed of rotation of said electrode being comprised between 1 and 100,000 g.

6. The process according to claim 4, wherein said polymer solution comprises carbon nanotubes at a concentration comprised between 0.00001 and 5% expressed in weight percent of said polymer solution before crosslinking.

7. The process according to claim 4, wherein said heat treatment step is followed by a step of treating the surface of said fibers, comprising bringing said network into the presence of a solution of at least one protein of the extracellular matrix or hyaluronic acid.

8. A device for cell support, comprising at least one network according to claim 1.

9. The infusible three-dimensional network of crosslinked polymer fibers according to claim 1, wherein the diameter of said fibers is comprised between 0.3 and 1 μm.

10. The infusible three-dimensional network of crosslinked polymer fibers according to claim 1, wherein the size of the interstices between said fibers is comprised between 0.5 and 10 μm$^2$.

11. The infusible three-dimensional network of crosslinked polymer fibers according to claim 1, wherein the stiffness of said network includes an elastic modulus comprised between 0.1 and 10,000 kPa.

12. The three-dimensional network according to claim 1, wherein the surface of the fibers is coated with at least one protein of the extracellular matrix.

13. The three-dimensional network according to claim 1, wherein the stiffness of the network includes an elastic modulus between 0.1 and 10,000 kPa.

14. The three-dimensional network according to claim 2, wherein said crosslinked polymer comprises nanofillers are carbon nanotubes.

15. The process for preparing a three-dimensional network of crosslinked polymer fibers according to claim 3, wherein in step a) the PAN solution is at a concentration of 10%, expressed in weight percent of said PAN solution.

16. The process for preparing a three-dimensional network of crosslinked polymer fibers according to claim 3, wherein in step b) said heat treatment under oxidizing atmosphere is at a temperature comprised between 200° C. and 300° C.

17. The process according to claim 4, wherein the PAN solution is extruded onto a drum.

18. The process according to claim 4, wherein said polymer solution comprises carbon nanotubes at a concentration comprised between 0.00001 and 1%.

19. The process according to claim 4, wherein said heat treatment step is followed by a step of treating the surface of said fibers, comprising bringing said network into the presence of a solution of at least one protein of the extracellular matrix, said bringing it into the presence being preceded by a prior treatment of the surface of the fibers of said network.

20. The process according to claim 4, wherein said at least one protein of the extracellular matrix is selected from: laminin, fibronectin, vitronectin and collagen.

\* \* \* \* \*